(12) United States Patent
Schoettgen et al.

(10) Patent No.: US 11,382,644 B2
(45) Date of Patent: Jul. 12, 2022

(54) SEALING AND CUTTING SURGICAL INSTRUMENT WITH ADVANCED FEEDBACK LOOP

(71) Applicant: Intuitive Surgical Operations, Inc., Sunnyvale, CA (US)

(72) Inventors: Benjamin J. Schoettgen, Sunnyvale, CA (US); David Robinson, Sunnyvale, CA (US); Pushkar Hingwe, Sunnyvale, CA (US); Patrick Flanagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 223 days.

(21) Appl. No.: 16/327,078

(22) PCT Filed: Aug. 22, 2017

(86) PCT No.: PCT/US2017/047929
§ 371 (c)(1),
(2) Date: Feb. 21, 2019

(87) PCT Pub. No.: WO2018/039181
PCT Pub. Date: Mar. 1, 2018

(65) Prior Publication Data
US 2019/0201022 A1  Jul. 4, 2019

Related U.S. Application Data

(60) Provisional application No. 62/377,995, filed on Aug. 22, 2016.

(51) Int. Cl.
*A61B 17/29* (2006.01)
*A61B 17/28* (2006.01)
(Continued)

(52) U.S. Cl.
CPC ........ *A61B 17/29* (2013.01); *A61B 17/07207* (2013.01); *A61B 18/1445* (2013.01);
(Continued)

(58) Field of Classification Search
CPC ........ A61B 2090/065; A61B 2090/067; A61B 17/29; A61B 17/28; A61B 2017/00115; A61B 2018/00601; A61B 2018/0063
See application file for complete search history.

(56) References Cited

U.S. PATENT DOCUMENTS 8,357,158 B2    1/2013   Mckenna et al.
2005/0256522 A1  11/2005  Francischelli et al.
(Continued)

OTHER PUBLICATIONS

International Search Report and Written Opinion for Application No. PCT/US2017/047929, dated Nov. 27, 2017, 16 pages.
(Continued)

*Primary Examiner* — Wade Miles
*Assistant Examiner* — Mohammed S Adam
(74) *Attorney, Agent, or Firm* — Kilpatrick Townsend & Stockton LLP

(57) ABSTRACT

Surgical instruments and assemblies for sealing and cutting tissue monitor jaw angle and/or jaw clamping force to provide feedback to an operator of the surgical instrument indicative of whether the tissue is suitable clamped for sealing and/or cutting. A surgical instrument or assembly includes a jaw operable to clamp tissue, a sealing mechanism, a cutting mechanism, an actuation monitoring assembly, and a feedback assembly. The actuation monitoring assembly monitors jaw angle and/or clamping force. The feedback assembly outputs feedback to the operator, based on the jaw angle and/or clamping force, as to whether the current clamping angle and/or jaw angle is suitable for sealing and/or clamping tissue.

10 Claims, 33 Drawing Sheets

(51) Int. Cl.
  *A61B 18/14* (2006.01)
  *A61B 17/072* (2006.01)
  *A61B 17/00* (2006.01)
  *A61B 90/00* (2016.01)
  *A61B 18/00* (2006.01)

(52) U.S. Cl.
  CPC ..... *A61B 17/28* (2013.01); *A61B 2017/00115* (2013.01); *A61B 2017/00734* (2013.01); *A61B 2018/0063* (2013.01); *A61B 2018/00601* (2013.01); *A61B 2018/1455* (2013.01); *A61B 2090/065* (2016.02); *A61B 2090/067* (2016.02); *A61B 2090/0811* (2016.02)

(56) References Cited

U.S. PATENT DOCUMENTS

| | | |
|---|---|---|
| 2010/0217264 A1 | 8/2010 | Odom et al. |
| 2012/0209314 A1 | 8/2012 | Weir et al. |
| 2015/0011996 A1 | 1/2015 | Brogna |
| 2015/0238268 A1 | 8/2015 | Weir et al. |
| 2016/0089175 A1* | 3/2016 | Hibner ................. A61B 17/285 606/206 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SEALING AND CUTTING SURGICAL INSTRUMENT WITH ADVANCED FEEDBACK LOOP

CROSS REFERENCE TO RELATED APPLICATIONS

The present application is a US National Stage application of PCT/US2017/047929 filed Aug. 22, 2017, which claims the benefit of U.S. Provisional Appln. No. 62/377,995 filed Aug. 22, 2016; the full disclosures which are incorporated herein by reference in their entirety for all purposes.

BACKGROUND

Sealing and cutting surgical instruments are used in many surgical procedures to seal tissue (e.g., via application of energy to fuse the tissue, via stapling) and to divide the sealed tissue via cutting. Many sealing and cutting surgical instruments include an end effector mounted at the distal end of an elongated instrument shaft and a proximal portion by which the proximal end of the instrument shaft is supported. The end effector typically includes a jaw for clamping tissue, a sealing mechanism for sealing the clamped tissue, and a cutting mechanism to cut the sealed tissue. The proximal portion typically includes a jaw actuation input member that is drivingly coupled with the jaw via a drive assembly and articulated to articulate the jaw. To seal and divide a tissue, the jaw is positioned to clamp the tissue, the jaw actuation input member is articulated to close the jaw to clamp the tissue, the instrument is operated to seal the tissue (e.g., a foot pedal is operated to apply energy to fuse the tissue, a stapler actuation input member is articulated to drive staples into the sealed tissue), and the instrument is operated to cut the sealed tissue (e.g., a cutting actuation input member is articulated to articulate a knife included in the end effector). Some embodiments of the instruments disclosed herein can be installed for use with a teleoperated surgical system, e.g., the da Vinci Surgical System commercialized by Intuitive Surgical of Sunnyvale, Calif.

Sealing and cutting surgical instruments, however, may be operated in ways that produce improperly sealed tissue and/or improperly cut tissue. For example, the operator may fail to properly clamp the tissue (e.g., under clamping, over clamping) prior to sealing the tissue. As another example, the jaw may be insufficiently closed to ensure proper cutting of the sealed tissue. Accordingly, improved sealing and cutting surgical instruments that reduce the occurrence of improperly sealed and/or cut tissue may help to improve surgical outcomes.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Sealing and cutting surgical instruments, and related methods, are provided that are configured to provide operational feedback to the operator of the instrument regarding whether jaw angle and/or clamping force are within suitable ranges for tissue sealing and/or cutting. In many embodiments, a sealing and cutting surgical instrument is configured to monitor jaw angle and/or clamping force and generate operational feedback based on the monitored jaw angle and/or clamping force. The operational feedback can indicate whether the jaw angle is greater than a maximum recommended angle for sealing tissue, the jaw angle is less than or equal to the maximum recommended angle for sealing tissue, the jaw angle is greater than a maximum recommended jaw angle for cutting tissue, the jaw angle is equal to or less than the maximum recommended angle for cutting tissue, the clamping force is less than a minimum recommended force for sealing tissue, and/or the clamping force is within a recommended range of clamping force for sealing tissue. In some embodiments, the instrument is configured to process jaw angles and associated clamping forces to determine characteristics of the clamped tissue (e.g., size, tissue stiffness) to determine a suitable value for minimum recommended clamping force for sealing tissue and/or a maximum recommended jaw angle for sealing tissue. The resulting operational feedback enhances the ability of the operator to properly operate the instrument, thereby helping to improve tissue sealing and/or cutting.

Thus, in one aspect, a surgical instrument for sealing and cutting tissue is provided that is configured to provide operational feedback. The surgical instrument includes an end effector including a jaw operable to clamp tissue, a sealing mechanism operable to seal tissue clamped by the jaw, a cutting mechanism operable to cut tissue clamped by the jaw, an actuation input member, an actuation monitoring assembly, and a feedback assembly. The actuation input member is drivingly coupled with the jaw and operable by an operator to articulate the jaw to clamp tissue. The actuation monitoring assembly is configured to generate at least one of a jaw-angle output indicative of a clamping angle of the jaw or a clamping-force output indicative of a clamping force of the jaw. The feedback assembly is configured to output to the operator, in response to at least one of the jaw-angle output or the clamping-force output, one or more indications including at least one of: (a) an indication that the clamping angle is greater than a maximum recommended clamping angle for sealing tissue clamped by the jaw, (b) an indication that the clamping angle is equal to or less than the maximum recommended clamping angle for sealing tissue clamped by the jaw, (c) an indication that the clamping angle is greater than a maximum recommended clamping angle for cutting tissue clamped by the jaw, (d) an indication that the clamping angle is equal to or less than the maximum recommended clamping angle for cutting tissue clamped by the jaw, (e) an indication that the clamping force is less than a minimum recommended clamping force for sealing tissue clamped by the jaw, and (f) an indication that the clamping force is equal to or greater than the minimum recommended clamping force for sealing tissue clamped by the jaw.

In some embodiments of the surgical instrument, the actuation monitoring assembly is configured to generate the jaw-angle output. The feedback assembly can be configured to, based on the jaw-angle output, output to the operator at least one of: (a) the indication that the clamping angle is greater than the maximum recommended clamping angle for sealing tissue clamped by the jaw, (b) the indication that the clamping angle is equal to or less than the maximum recommended clamping angle for sealing tissue clamped by the jaw, (c) the indication that the clamping angle is greater than the maximum recommended clamping angle for cutting tissue clamped by the jaw, and (d) the indication that the clamping angle is equal to or less than the maximum recommended clamping angle for cutting tissue clamped by the jaw.

In some embodiments of the surgical instrument, the actuation monitoring assembly is configured to generate the clamping-force output. The feedback assembly can be configured to, based on the clamping-force output, output to the operator at least one of: (a) the indication that the clamping force is less than the minimum recommended clamping force for sealing tissue clamped by the jaw, and (b) the indication that the clamping force is equal to or greater than the minimum recommended clamping force for sealing tissue clamped by the jaw.

In some embodiments of the surgical instrument, the actuation monitoring assembly is configured to generate the jaw-angle output and the clamping-force output. The feedback assembly can be configured to, based on the jaw-angle output and the clamping-force output, output to the operator at least one of: (a) the indication that the clamping force is less than the minimum recommended clamping force for sealing tissue clamped by the jaw; and (b) the indication that the clamping force is equal to or greater than the minimum recommended clamping force for sealing tissue clamped by the jaw. The feedback assembly can include a control unit configured to: (a) monitor the jaw-angle output and the clamping-force output to identify an initial contact jaw angle corresponding to initial contact between the jaw and tissue clamped by the jaw, and (b) select the maximum recommended clamping angle for sealing tissue clamped by the jaw based on the initial contact jaw angle. The control unit can be configured to: (a) process the jaw-angle output and the clamping-force output to determine a tissue stiffness of the tissue clamped by the jaw, and (b) select the maximum recommended clamping angle for sealing tissue clamped by the jaw based on the tissue stiffness.

The surgical instrument can include any suitable one or more output elements configured to output the one or more indications to the operator. For example, the one or more output elements can include one or more of: (a) one or more indicator lights, (b) an output display, and (c) an aural output device.

The surgical instrument can include a spring assembly configured to inhibit application of an excessive clamping force to tissue clamped by the instrument. In some embodiments, the spring assembly includes an output link drivingly coupled with the jaw, an input link drivingly coupled with the actuation input member, and a spring coupled with the input and output links to transfer an articulation force from the input link to the output link to induce a grip force of the jaw. The spring can be preloaded to inhibit relative movement between the input link and the output link while the transferred articulation force is below a predetermined level and to allow relative movement between the input link and the output link when the transferred articulation force is above the predetermined level.

The surgical instrument can be configured to control enablement of supply of a sealing energy to the surgical instrument for sealing tissue clamped by the jaw. For example, the surgical instrument can include a sealing enablement output configured to output a sealing enablement signal for controlling enablement of supply of the sealing energy to the surgical instrument for sealing tissue clamped by the jaw. The sealing enablement signal can be indicative of at least one of: (a) the clamping angle is greater than the maximum recommended clamping angle for sealing tissue clamped by the jaw, (b) the clamping angle is equal to or less than the maximum recommended clamping angle for sealing tissue clamped by the jaw, (c) the clamping force is less than the minimum recommended clamping force for sealing tissue clamped by the jaw, and (d) the clamping force is equal to or greater than the minimum recommended clamping force for sealing tissue clamped by the jaw.

In another aspect, a method is provided for generating feedback to an operator of a surgical instrument configured for sealing and cutting tissue. The method includes articulating a jaw of an end effector included in the surgical instrument from an open configuration towards a closed configuration to clamp tissue. An actuation monitoring assembly included in the surgical instrument generates at least one of a jaw-angle output indicative of a clamping angle of the jaw or a clamping-force output indicative of a clamping force of the jaw. A feedback assembly included in the surgical instrument outputs at least one of: (a) an indication to the operator that the clamping angle is greater than a maximum recommended clamping angle for sealing tissue clamped by the jaw, (b) an indication to the operator that the clamping angle is equal to or less than the maximum recommended clamping angle for sealing tissue clamped by the jaw, (c) an indication to the operator that the clamping angle is greater than a maximum recommended clamping angle for cutting tissue clamped by the jaw, (d) an indication to the operator that the clamping angle is equal to or less than the maximum recommended clamping angle for cutting tissue clamped by the jaw, (e) an indication to the operator that the clamping force is less than a minimum recommended clamping force for sealing tissue clamped by the jaw, and (f) an indication to the operator that the clamping force is equal to or greater than the minimum recommended clamping force for sealing tissue clamped by the jaw.

The method for generating feedback to an operator of the surgical instrument can include generating, with the actuation monitoring assembly, the jaw-angle output and the clamping-force output. The control unit can process the jaw-angle output and the clamping-force output to identify an initial contact jaw angle corresponding to initial contact between the jaw and tissue clamped by the jaw. The control unit can select the maximum recommended clamping angle for sealing tissue clamped by the jaw based on the initial contact jaw angle. The control unit can process the jaw-angle output and the clamping-force output to determine a tissue stiffness of the tissue clamped by the jaw. The control unit can select the maximum recommended clamping angle for sealing tissue clamped by the jaw based on the tissue stiffness.

In some embodiments of the method for generating feedback to the operator of the surgical instrument, the feedback assembly includes one or more output elements configured to output the one or more indications to the operator. The one or more output elements can include at least one of: (a) one or more indicator lights, (b) an output display, and (c) an aural output device.

In some embodiments of the method for generating feedback to the operator of the surgical instrument, the surgical instrument includes a spring assembly configured to inhibit application of an excessive clamping force to tissue clamped by the instrument. In some embodiments of the method, the spring assembly includes an output link drivingly coupled with the jaw, an input link drivingly coupled with the actuation input member, and a spring coupled with the input and output links to transfer an articulation force from the input link to the output link to induce a grip force of the jaw. The spring can be preloaded to inhibit relative movement between the input link and the output link while the transferred articulation force is below a predetermined level and to allow relative movement between the input link and the output link when the transferred articulation force is above the predetermined level.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Surgical instruments and assemblies for sealing and cutting tissue are provided that monitor jaw angle and/or jaw clamping force of an end effector used to seal and cut the tissue and output an indication(s) to the operator (via one or more suitable feedback elements such as one or more output lights, a suitable output display such as a liquid crystal display (LCD), or an aural output device such as a speaker) whether or not the current jaw angle and/or jaw clamping force is suitable for sealing tissue clamped by the jaw and/or cutting tissue clamped by the jaw. As a result of the feedback, the operator is provided information that may help the operator to make better decisions such as to whether to proceed with sealing the tissue, whether to proceed with cutting the tissue, or whether to re-grasp the tissue.

Figure 1:
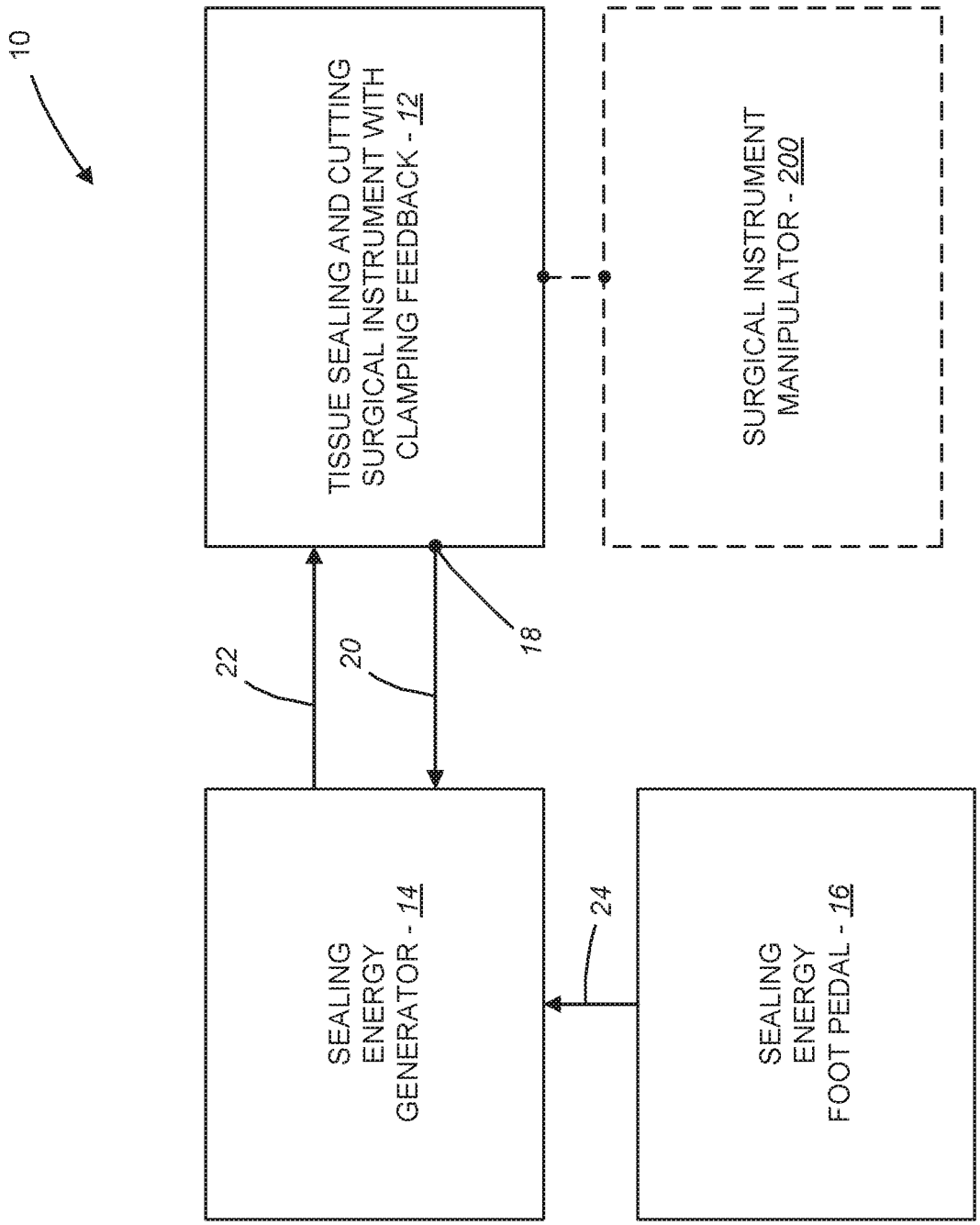
FIG. 1 is a simplified schematic diagram of a tissue sealing and cutting system, in accordance with many embodiments.

Turning now to the drawing figures in which like reference indicators refer to like elements in the various figures, FIG. 1 is a simplified schematic diagram of a tissue sealing and cutting system 10, in accordance with many embodiments. The tissue sealing and cutting system 10 includes a tissue sealing and cutting surgical instrument 12 with clamping feedback, a sealing energy generator 14, and a sealing energy foot pedal 16. In some embodiments, the tissue sealing and cutting system 10 further includes a surgical instrument manipulator 200 configured for mounting of the surgical instrument 12 to the manipulator 200 and operable to controllably manipulate the surgical instrument 12 under the control of an operator of the manipulator 200. The surgical instrument 12 includes an end effector configured to grasp tissue, clamp the grasped tissue, seal the clamped tissue, and cut the sealed and clamped tissue.

The system 10 is configured to monitor a jaw angle of the end effector and/or a clamping force of the end effector and to provide feedback based on the jaw angle and/or the clamping force. For example, the system 10 can be configured to output one or more indications to an operator of the surgical instrument 12 regarding whether the jaw angle and/or the clamping force is suitable for sealing tissue clamped by the end effector. The system 10 can be configured to output one or more indications to the operator regarding whether the jaw angle is suitable for cutting tissue clamped by the end effector. In some embodiments, the system 10 includes one or more output elements (e.g., one or more output lights, an output display, an aural output device) for outputting the one or more indications to the operator regarding whether the jaw angle and/or the clamping force is suitable for sealing and/or cutting tissue clamped by the end effector. For example, the system 10 can be configured to output, via the one or more output elements, at least one of: (a) an indication to the operator that the clamping angle is greater than a maximum recommended clamping angle for sealing tissue clamped by the jaw, (b) an indication to the operator that the clamping angle is equal to or less than the maximum recommended clamping angle for sealing tissue clamped by the jaw, (c) an indication to the operator that the clamping angle is greater than a maximum recommended clamping angle for cutting tissue clamped by the jaw, (d) an indication to the operator that the clamping angle is equal to or less than the maximum recommended clamping angle for cutting tissue clamped by the jaw, (e) an indication to the operator that the clamping force is less than a minimum recommended clamping force for sealing tissue clamped by the jaw, or (f) an indication to the operator that the clamping force is equal to or greater than the minimum recommended clamping force for sealing tissue clamped by the jaw.

In the illustrated embodiment, the surgical instrument 12 includes a sealing enablement output 18 and is configured to output a sealing enablement signal 20 for controlling enablement of supply of sealing energy 22 from the sealing energy generator 14 to the surgical instrument 12 for sealing tissue clamped by the end effector. The sealing enablement signal 20 can be indicative of at least one of: (a) the clamping angle is greater than the maximum recommended clamping angle for sealing tissue clamped by the jaw, (b) the clamping angle is equal to or less than the maximum recommended clamping angle for sealing tissue clamped by the jaw, (c) the clamping force is less than the minimum recommended clamping force for sealing tissue clamped by the jaw, or (d) the clamping force is equal to or greater than the minimum recommended clamping force for sealing tissue clamped by the jaw.

In the illustrated embodiment, the sealing energy foot pedal 16 is configured to output an operator controlled enablement signal 24 to the sealing energy generator 14. The sealing energy generator 14 can be configured to output the sealing energy 22 to the surgical instrument 12 at a suitable power level over a suitable time span in response to any suitable combination of the sealing enablement signal 20 generated by the surgical instrument 12 and the operator controlled enablement signal 24 generated by the sealing energy foot pedal 16. For example, the sealing energy generator 14 can be configured to output the sealing energy 22 when the sealing enablement signal 20 indicates suitable jaw angle and/or jaw clamping pressure for sealing tissue clamped by the end effector, when the operator controlled enablement signal 24 is generated by the sealing energy foot pedal 16, or when both the sealing enablement signal 20 indicates suitable jaw angle and/or jaw clamping force for sealing tissue clamped by the end effector and the operator controlled enablement signal 24 is generated by the sealing energy foot pedal 16.

The surgical instrument manipulator 200 can have any suitable configuration for manipulation of the surgical instrument 12 under the control of an operator. For example, the manipulator 200 can be included in a robotic surgical system including an operator's console by which an operator controls operation of the manipulator 200 and thereby the surgical instrument mounted to the manipulator 200. The manipulator 200 can be mounted to any suitable base, which can be secured in a fixed position and orientation relative to a patient on which a surgical procedure is performed via the system 10. For example, the base can be (or attached to) an operating table supporting the patient. As another example, the manipulator 200 can be included in a patient side robotic assembly that can be secured in a fixed position and orientation relative to the patient.

Figure 2:
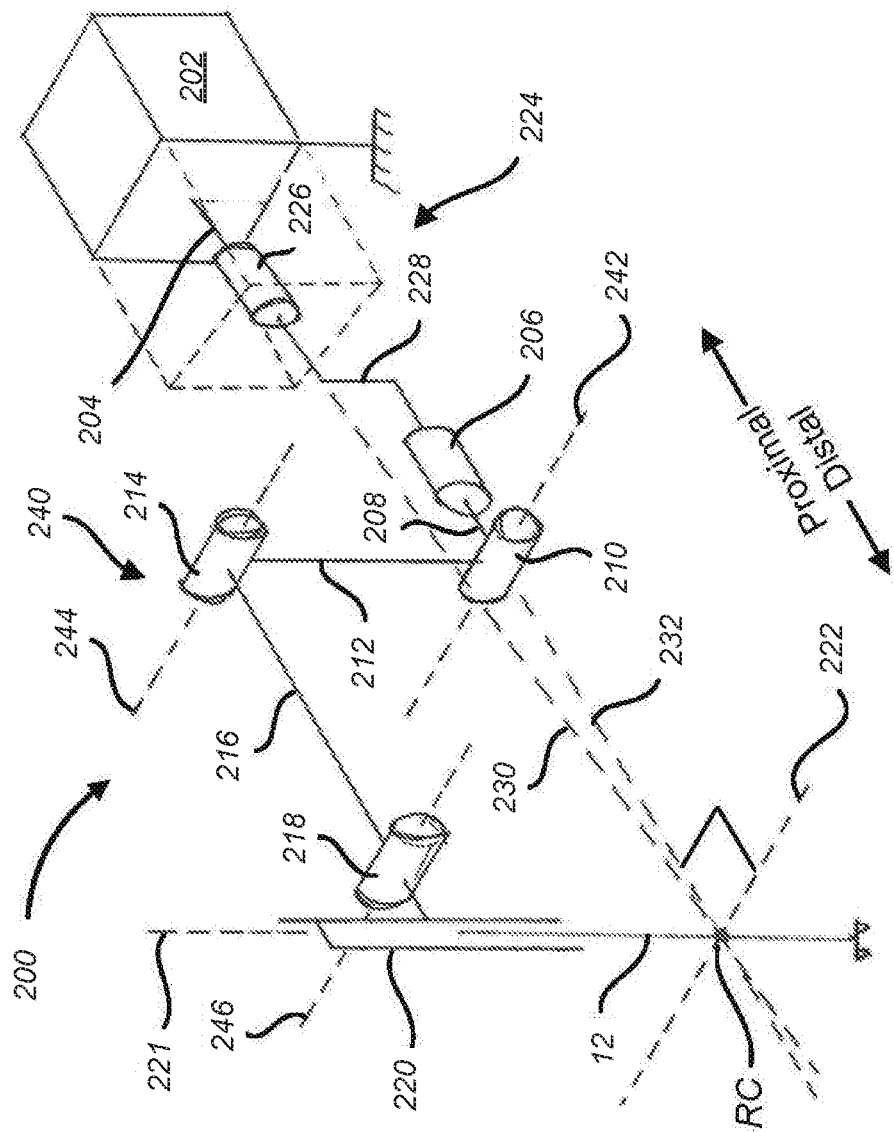
FIG. 2 is a perspective schematic representation of a surgical instrument manipulator, in accordance with some embodiments, that can be employed in the tissue sealing and cutting system of FIG. 1.

FIG. 2 is a perspective schematic representation of an embodiment of the surgical instrument manipulator 200. The manipulator 200 includes a mounting base 202, a base link 204, a yaw joint 206, an extension link 208, a base parallelogram joint 210, a first parallelogram link 212, a first parallelogram joint 214, a second parallelogram link 216, a second parallelogram joint 218, and an instrument holder 220. The surgical instrument 12 can be configured to be detachably mounted to the instrument holder 220, which can be configured to translate the surgical instrument 12 along an insertion axis 221 that is parallel to an elongated instrument shaft of the surgical instrument 12 to insert the instrument shaft into a patient through a remote center of manipulation (RC) that is fixed relative to the patient.

The illustrated embodiment of the manipulator 200 includes a conical sweep mechanism 224. The conical sweep mechanism 224 includes a conical sweep joint 226 and a conical sweep link 228 that is rotationally coupled to the base link 204 by the conical sweep joint 226. The conical sweep joint 226 is operable to selectively rotate the conical sweep link 228 around a conical sweep axis 230 that intersects the RC. The distal end of the conical sweep link 228 supports the yaw joint 206. The yaw joint 206 rotationally couples the extension link 208 to the conical sweep link 228 for rotation of the extension link about a yaw axis 232 that intersects the RC. The conical sweep link 228 is configured to position and orient the yaw joint 206 such that the yaw axis 232 intersects the RC for all orientations of the conical sweep link 228 around the conical sweep axis 230. The conical sweep mechanism 224 is operable to reorient the outboard linkage of the manipulator 200 relative to the mounting base 202 while maintaining the position of the RC relative to the mounting base 202. Rotation of conical sweep joint 226 causes the shaft of surgical instrument 12 to sweep along the surface of a cone centered on the conical sweep axis 230 and having a vertex at the RC. The conical sweep mechanism 224 can be used in any suitable fashion, for example, as a set-up joint that is used to position/orient the outboard portion of the manipulator 200 prior to a surgical procedure and/or used to position/orient the outboard portion of the manipulator 200 actively during a surgical procedure. The conical sweep axis 230 provides a redundant degree of freedom axis about which the instrument holder 220 can be rotated around the RC. The conical sweep axis 230 is not aligned with any of the yaw axis 232, the pitch axis 222, or the insertion axis 221. The conical sweep axis 230 can be offset from the yaw axis 232 by any suitable angle (e.g., 15 degrees in one embodiment). The conical sweep mechanism 224 is optional and may be omitted in some embodiments of the manipulator 200.

A parallelogram linkage portion 240 of the manipulator 200 is configured to produce motion of the instrument holder 220 that is limited to rotation about a pitch axis 222. By limiting the corresponding movement of the instrument holder 220 to rotation (pitch) about the pitch axis 222, the insertion axis 221 continually intersects the RC and the distance between the instrument holder 220 and the RC is maintained.

The parallelogram linkage portion 240 includes the parallelogram base joint 210, the first parallelogram link 212, the first parallelogram joint 214, the second parallelogram link 216, the second parallelogram joint 218, and the instrument holder 220. The base parallelogram joint 210 rotationally couples the proximal end of the first parallelogram link 212 to the distal end of the extension link 208. The base parallelogram joint 210 is operable to produce controlled rotation of the first parallelogram link 212 about a base joint axis 242 that is parallel to the pitch axis 222. The position and orientation of the base joint axis 242 is fixed relative to the extension link 208. The first parallelogram joint 214 rotationally couples the proximal end of the second parallelogram link 216 to the distal end of the first parallelogram link 212 for rotation of the second parallelogram link 216 about a first joint axis 244 that is parallel to the pitch axis 222. The position and orientation of the first joint axis 244 is fixed relative to the first parallelogram link 212. The second parallelogram joint 218 rotationally couples the instrument holder 220 to the distal end of the second parallelogram link 216 for rotation of the instrument holder 220 about a second joint axis 246 that is parallel to the pitch axis 222. The position and orientation of the second joint axis 246 is fixed relative to the second parallelogram link 216.

The first and second parallelogram joints 214, 218 are rotationally coupled to the base parallelogram joint 210 so that actuation of the base parallelogram joint 210 actuates the parallelogram linkage portion 240, thereby generating corresponding motion of the instrument holder 220 that is limited to rotation about the pitch axis 222. Any suitable approach can be used to rotationally couple the base parallelogram joint 210, the first parallelogram joint 214, and the second parallelogram joint 218. For example, the base parallelogram joint 210 can include a base pulley that is rotationally fixed to the extension link 208 and mounted to rotate relative to the first parallelogram link 212 around the base joint axis 242. The first parallelogram joint 214 can include a first pulley that is rotationally fixed to the second parallelogram link 216 and mounted to rotate relative to the first parallelogram link 212 around the first joint axis 244. By tying the rotation of the first pulley to rotation of the second pulley, for example by one or more drive belts or one or more links, rotation of the second parallelogram link 216 relative to the first parallelogram link 212 can be driven by rotation of the first parallelogram link 212 relative to the extension link 208 such that the same relative orientation between the second parallelogram link 216 and the extension link 208 is maintained for all angular orientation of the first parallelogram link 212 relative to the extension link 208. In a like manner, the first parallelogram joint 214 can include a third pulley that is rotationally fixed to the first parallelogram link 212 and mounted to rotate relative to the second parallelogram link 216 around the first joint axis 244. The second parallelogram joint 218 can include a fourth pulley that is rotationally fixed to the instrument holder 220 and mounted to rotate relative to the second parallelogram link 216 around the second joint axis 246. By tying the rotation of the third pulley to rotation of the fourth pulley, for example by one or more drive belts or one or more links, rotation of the instrument holder 220 relative to the second parallelogram link 216 can be driven by rotation of the second parallelogram link 216 relative to the first parallelogram link 212 such that the same relative orientation between the insertion axis 221 and the first parallelogram link 212 is maintained for all angular orientation of the second parallelogram link 216 relative to the first parallelogram link 212.

Figure 3:
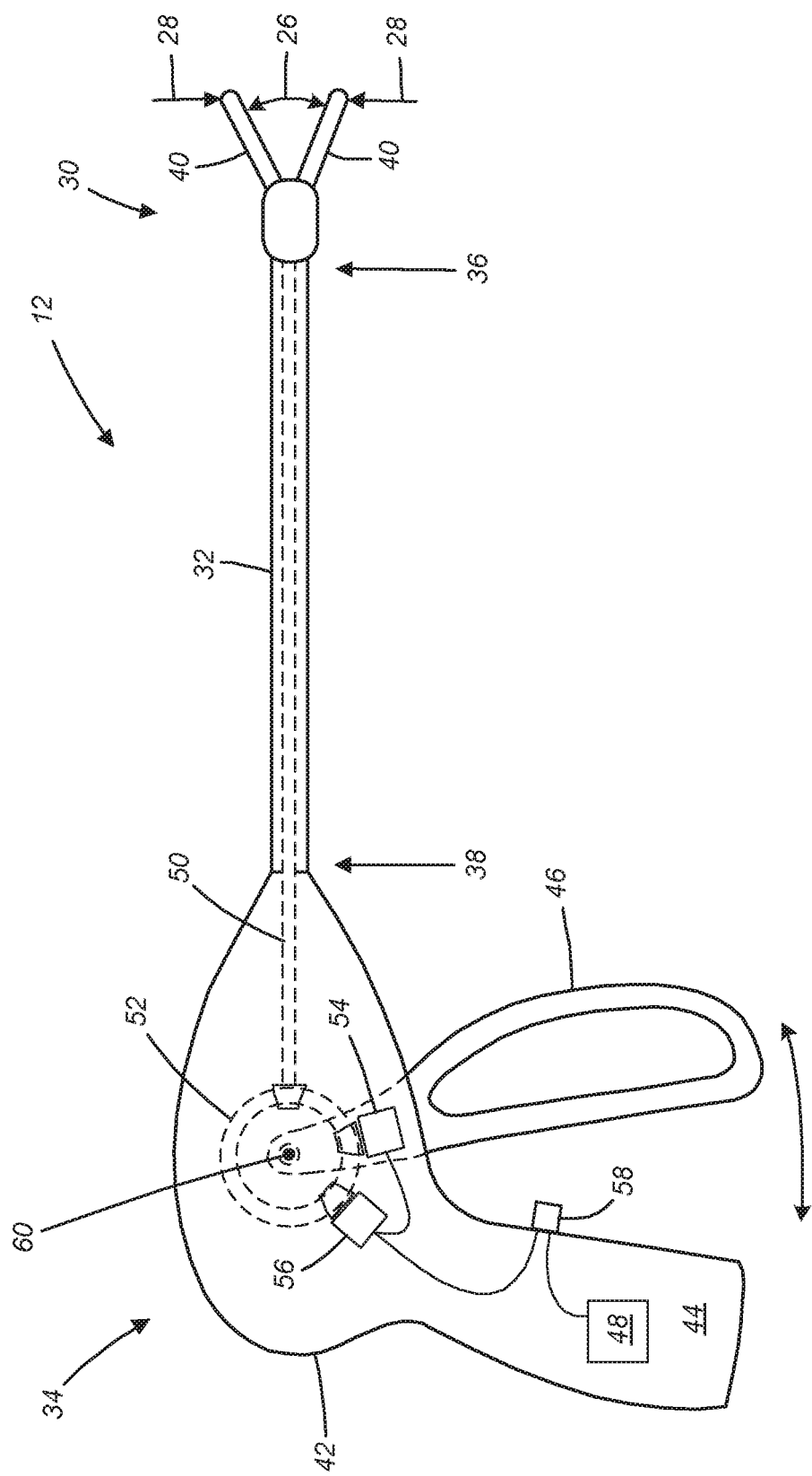
FIG. 3 illustrates a hand held surgical instrument for tissue sealing and/or cutting, in accordance with some embodiments.

FIG. 3 illustrate an embodiment of the hand held surgical instrument 12 configured to clamp tissue, seal the clamped tissue, and cut the sealed and clamped tissue, in accordance with some embodiments. As described herein with respect to various embodiments, the surgical instrument 12 can further include components for monitoring jaw angle 26 and/or jaw clamping force 28 and to provide feedback regarding whether jaw angle 26 and/or jaw clamping force 28 is/are suitable for sealing and/or cutting tissue, in accordance with some embodiments. The surgical instrument 12 includes an end effector 30, an elongated instrument shaft 32, and a proximal assembly 34. The end effector 30 is mounted to a distal end 36 of the instrument shaft 32. A proximal end 38 of the instrument shaft 32 is mounted to the proximal assembly 34. The end effector 30 includes one or more jaws 40 that can be actuated to grasp and clamp tissue.

The proximal assembly 34 is configured to be held and manipulated by an operator of the surgical instrument 12 so as to accomplish sealing and cutting of a tissue. The proximal assembly 34 includes a housing 42 that includes a handle portion 44, an actuation input member 46, a battery 48, a drive shaft 50, a main gear 52, an input ratchet mechanism 54, a detent ratchet mechanism 56, and a clamping reset button 58. The one or more jaws 40 are drivingly coupled with the drive shaft 50 so that rotation of the drive shaft 50 in one direction closes the jaws 40 and rotation of the drive shaft 50 in the opposite direction opens the jaws 40. The drive shaft 50 is drivingly coupled with the main gear 52, which is rotatable via articulation of the actuation input member 46 by the operator of the surgical instrument 12. The actuation input member 46 is pivotally mounted to the housing 42 for operator induced limited rotation of the actuation input member 46 about an axis 60 relative to the housing 42 between an un-squeezed position (the illustrated position) of the actuation input member 46 and a squeezed position of the actuation input member 46 disposed closer to the handle portion 44. The input ratchet mechanism 54 is mounted to the actuation input member 46 and is configured to interface with the main gear 52 and cause rotation of the main gear 52 when the actuation input member 46 is pulled towards the handle portion 44 from the un-squeezed position to the squeezed position and allow resetting of the actuation input member 46 back to the un-squeezed position from the squeezed position without causing rotation of the main gear 52. In some embodiments, the proximal portion 34 includes a torsion spring (not shown) that biases the actuation input member 46 towards the un-squeezed position. The detent ratchet mechanism 56 is mounted to the housing 42 and is configured to accommodate rotation of the main gear 52 when the main gear 52 is rotated via motion of the actuation input member 46 from the un-squeezed position to the squeezed position and prevent back rotation of the main gear 52 during motion of the actuation input member 46 from the squeezed position back to the un-squeezed position. Accordingly, repeated squeezing and releasing of the actuation input member 46 by the operator of the surgical member 12 can be used to incrementally articulate the end effector 30 to incrementally close the jaws 40 to clamp tissue.

The input ratchet mechanism 54 and the detent ratchet mechanism 56 are controllable to induce articulation of the end effector 30 to open the jaws 40. In the illustrated embodiment, the clamping reset button 58 is operably connected to the battery 48 and supplies a voltage to each of the input ratchet mechanism 54 and the detent ratchet mechanism 56 upon actuation of the clamping reset button 58 to actuate a solenoid included in each of the ratchet mechanisms 54, 56 to reconfigure the ratchet mechanism 54, 56 to accommodate back rotation of the main gear 52 to rotate the drive shaft 50 so as to actuate the end effector 30 to open the jaws 40. In some embodiments, the proximal portion 34 includes another torsion spring (not shown) that biases the main gear 52 in one rotational direction to bias the end effector 30 to open the jaws 40 when the clamping reset button 58 is actuated.

Figure 4:
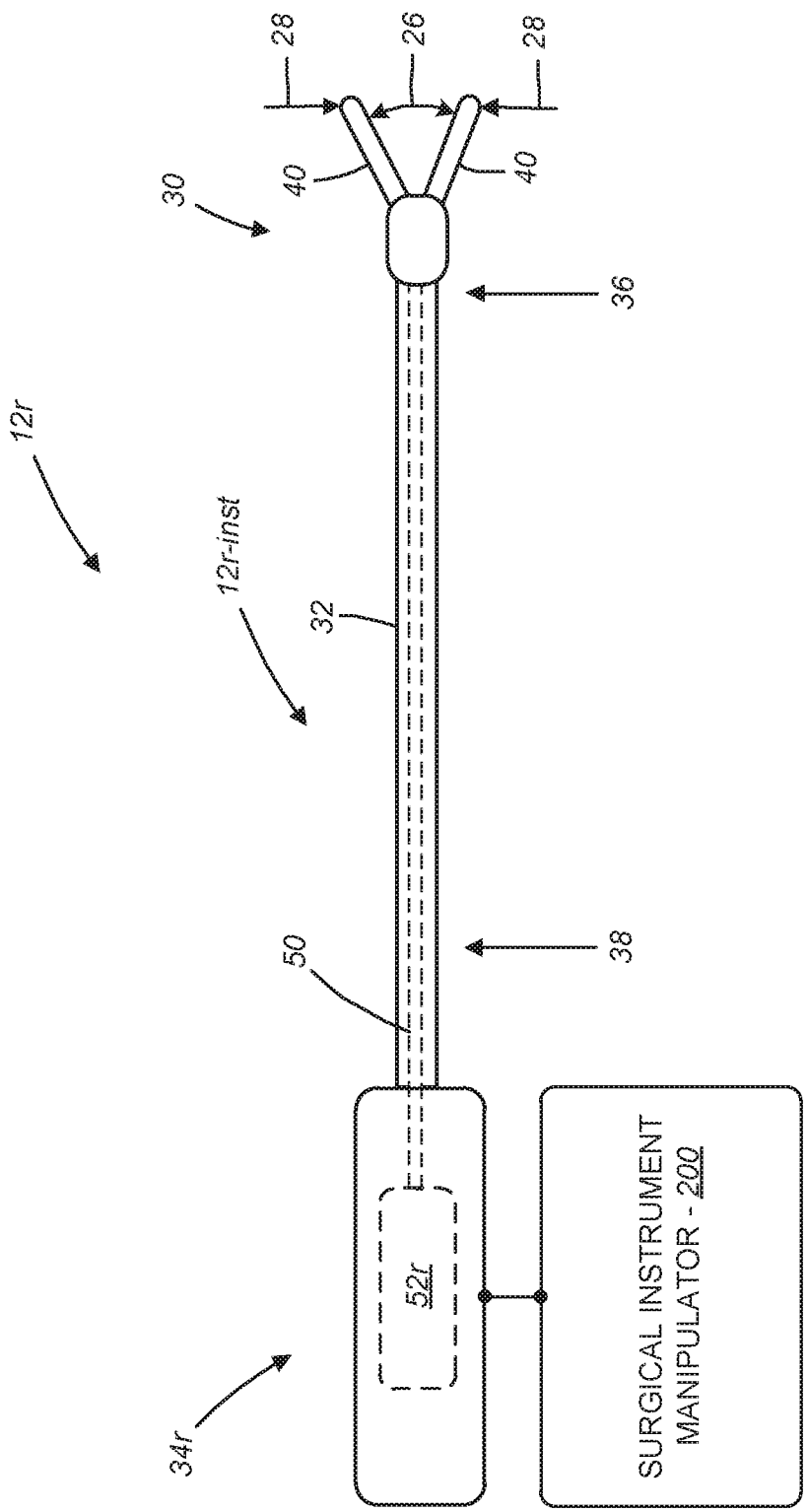
FIG. 4 illustrates a surgical assembly for tissue sealing and/or cutting, in accordance with some embodiments.

FIG. 4 illustrates a surgical assembly 12r for tissue sealing and/or cutting, in accordance with some embodiments. The surgical assembly 12r is configured similar to the surgical instrument 12, but includes a surgical instrument 12r-inst and the manipulator 200 to which the surgical instrument 12r-inst is detachably mountable. The surgical instrument 12r-inst includes a proximal assembly 34r that is configured to be detachably mountable to the manipulator 200. The surgical assembly 12r includes components similar to components of the surgical instrument 12 with the similar components being designated by the same or similar reference numbers and the description of such components of the surgical instrument 12 being applicable to the respective components of the surgical assembly 12r.

The surgical instrument 12r-instr includes a drive assembly 52r that is drivingly coupled with the drive shaft 50. In some embodiments, the drive assembly 52r includes a drive input coupler that drivingly couples with a drive output coupler of the manipulator 200 when the surgical instrument 12r-inst is mounted to the manipulator 200. In such embodiments, the drive input coupler is drivingly coupled with the drive shaft 50 via the drive assembly 52r. In other embodiments, the drive assembly 52r includes a motor that is drivingly coupled with the drive shaft 50 and operable to controllably rotate the drive shaft 50 to open and close the jaws 40 in accordance with a control input received from an operator of the surgical assembly 12r.

The surgical instrument 12r-inst may be configured to clamp tissue, seal the clamped tissue, and cut the sealed and clamped tissue. The manipulator 200 and/or the drive assembly 52r can include components for monitoring the jaw angle 26 and/or the jaw clamping force 28 and to provide feedback regarding whether the jaw angle 26 and/or the jaw clamping force 28 is/are suitable for sealing and/or cutting tissue, in accordance with some embodiments. The proximal end 38 of the instrument shaft 32 is mounted to the proximal assembly 34r.

Figure 5:
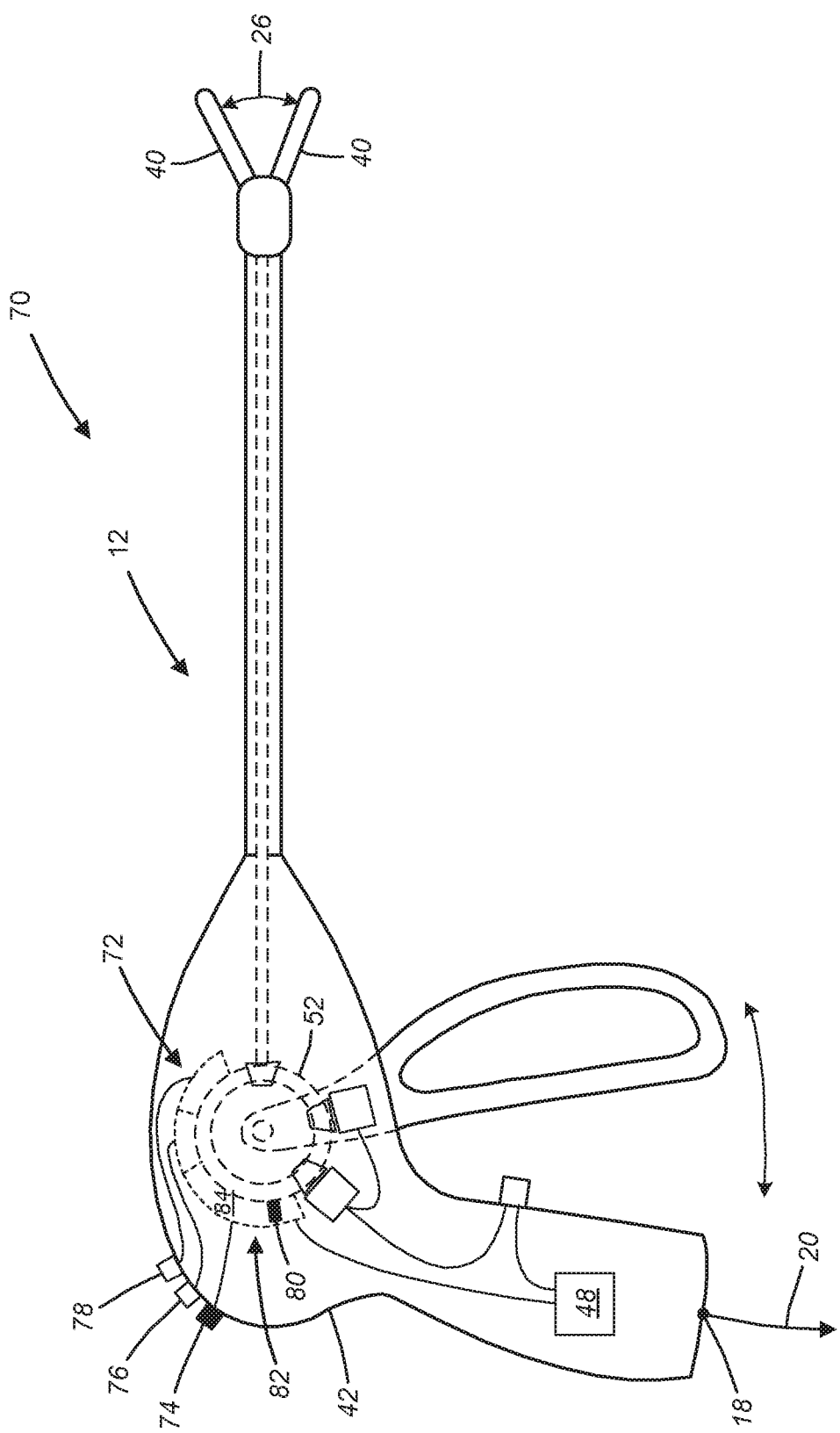
FIG. 5, FIG. 6, and FIG. 7 illustrate a hand held surgical instrument that is configured to provide feedback regarding whether jaw angle is suitable for tissue sealing and/or cutting, in accordance with some embodiments.
Figure 6:
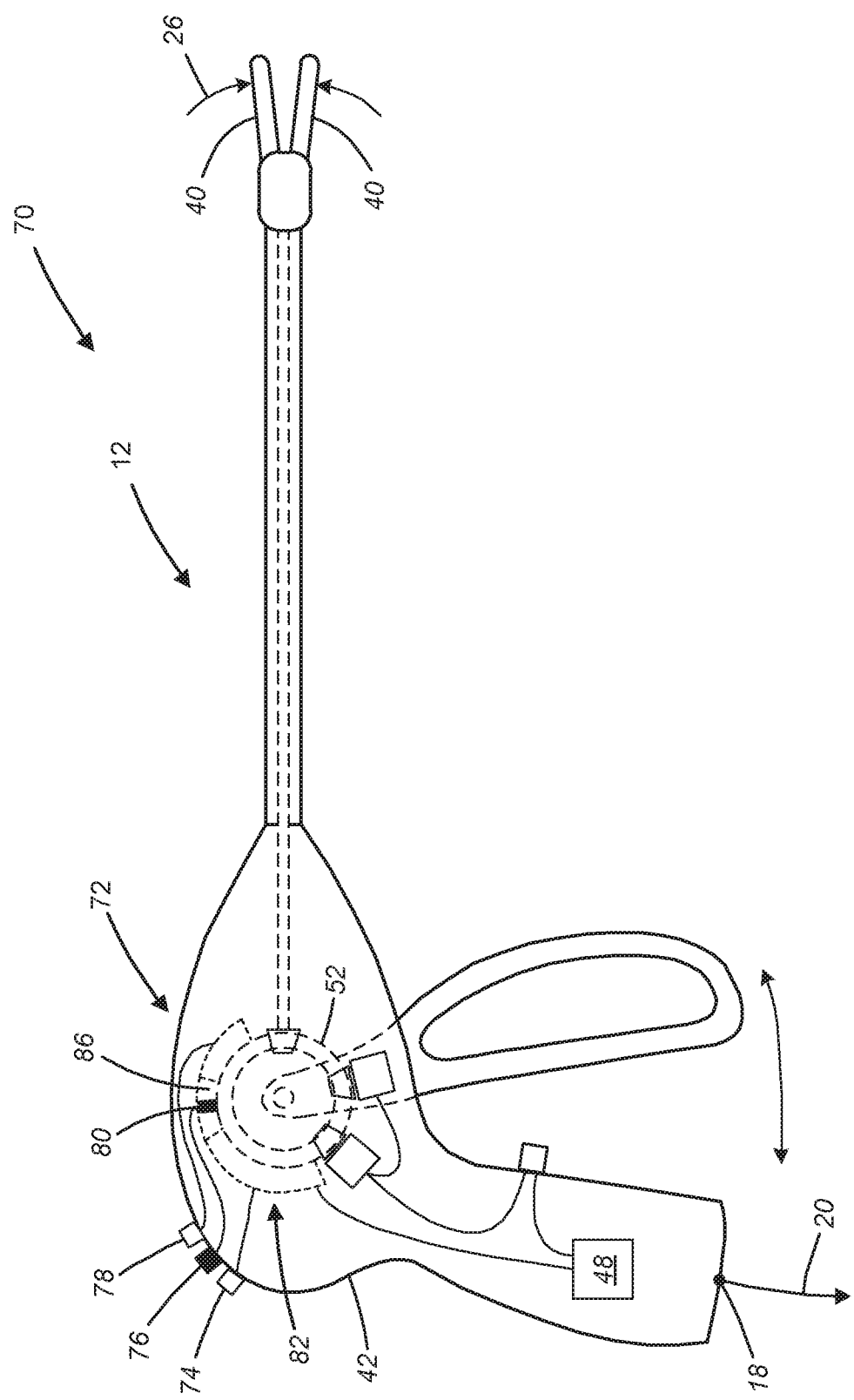
Figure 7:
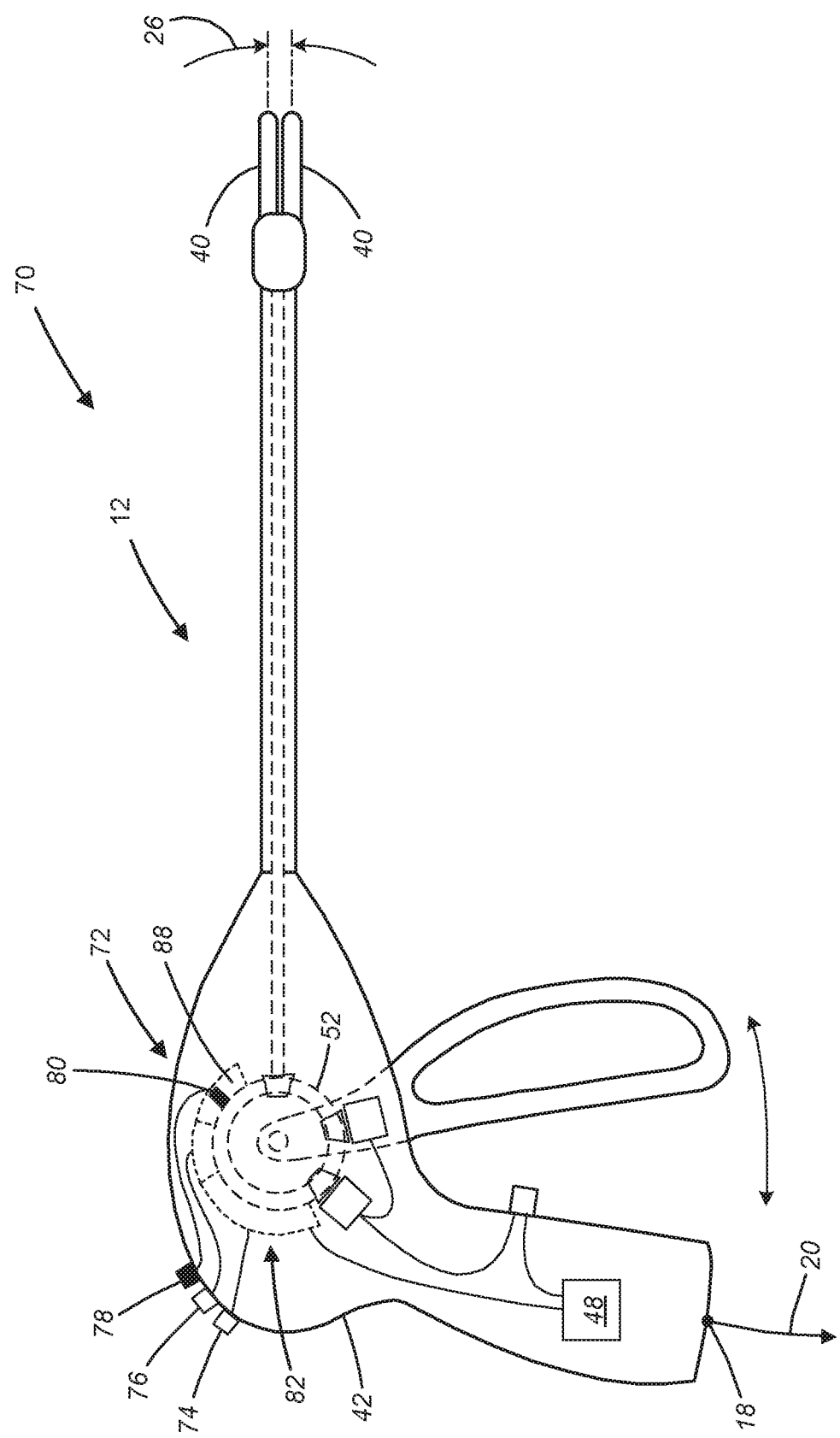

FIG. 5, FIG. 6, and FIG. 7 illustrate a hand held surgical instrument 70 that is configured to provide feedback regarding whether jaw angle is suitable for tissue sealing and/or cutting, in accordance with some embodiments. The surgical instrument 70 includes the surgical instrument 12 and an actuation monitoring assembly 72. The surgical instrument 70 can include one or more of feedback output lights 74, 76, 78 and/or the sealing enablement output 18. The surgical instrument 70 is configured to provide operational feedback regarding the current jaw angle 26 of the jaws 40, for example, via one or more of the feedback output lights 74, 76, 78 and/or the sealing enablement output 18. Each of the output lights 74, 76, 78 can be operatively connected to the actuation monitoring assembly 72, which is operatively coupled with the battery 48. The actuation monitoring assembly 72 includes a main gear element 80 mounted to the main gear 52 and a position detecting element 82 mounted to the housing 42. As illustrated in FIG. 3, the position detecting element 82 includes a first position detecting portion 84 configured to transmit battery voltage to energize the output light 74 when the main gear 52 is oriented to position the main gear element 80 within the rotational sector covered by the first position detecting portion 84. Output light 74 provides an indication to the operator of the surgical instrument 70 that the current jaw angle 26 of the jaws 40 is greater than a maximum recommended angle for sealing tissue clamped by the jaws 40 and greater than a maximum recommended angle for cutting tissue clamped by the jaws 40. As illustrated in FIG. 4, the position detecting element 82 includes a second position detecting portion 86 configured to transmit battery voltage to energize the output light 76 when the main gear 52 is oriented to position the main gear element 80 within the rotational sector covered by the second position detecting portion 86. The output light 76 provides an indication to the operator of the surgical instrument 70 that the current jaw angle 26 of the jaws 40 is equal to or less than the maximum recommended angle for sealing tissue clamped by the jaws 40 but is still greater than the maximum recommended angle for cutting tissue clamped by the jaws 40. As illustrated in FIG. 5, the position detecting element 82 includes a third position detecting portion 88 configured to transmit battery voltage to energize the output light 78 when the main gear 52 is oriented to position the main gear element 80 within the rotational sector covered by the third position detecting portion 88. The output light 78 provides an indication to the operator of the surgical instrument 70 that the current jaw angle 26 of the jaws 40 is less than the maximum recommended angle for sealing tissue clamped by the jaws 40 and is equal to or less than the maximum recommended angle for cutting tissue clamped by the jaws 40.

The surgical instrument 70 can be configured to include the sealing enablement output 18 and output the sealing enablement signal 20. The sealing enablement output 18 can be operatively connected with the second and third position detecting portions 86, 88 of the position detecting element 82 so that the battery voltage is applied to the sealing enablement output 18 when the orientation of the main gear 52 positions the main gear element 80 within the combined rotational sector covered by the second and third position detecting portions 86, 88. With the surgical instrument 70, the sealing enablement signal 20 can be indicative of at least one of: (a) the current jaw angle 26 is greater than the maximum recommended clamping angle for sealing tissue clamped by the jaws 40, or (b) the current jaw angle 26 is equal to or less than the maximum recommended clamping angle for sealing tissue clamped by the jaws 40. When configured to include the sealing enablement output 18, the surgical instrument 70 can be used in the tissue sealing and cutting system 10 in lieu of the surgical instrument 12.

Figure 8:
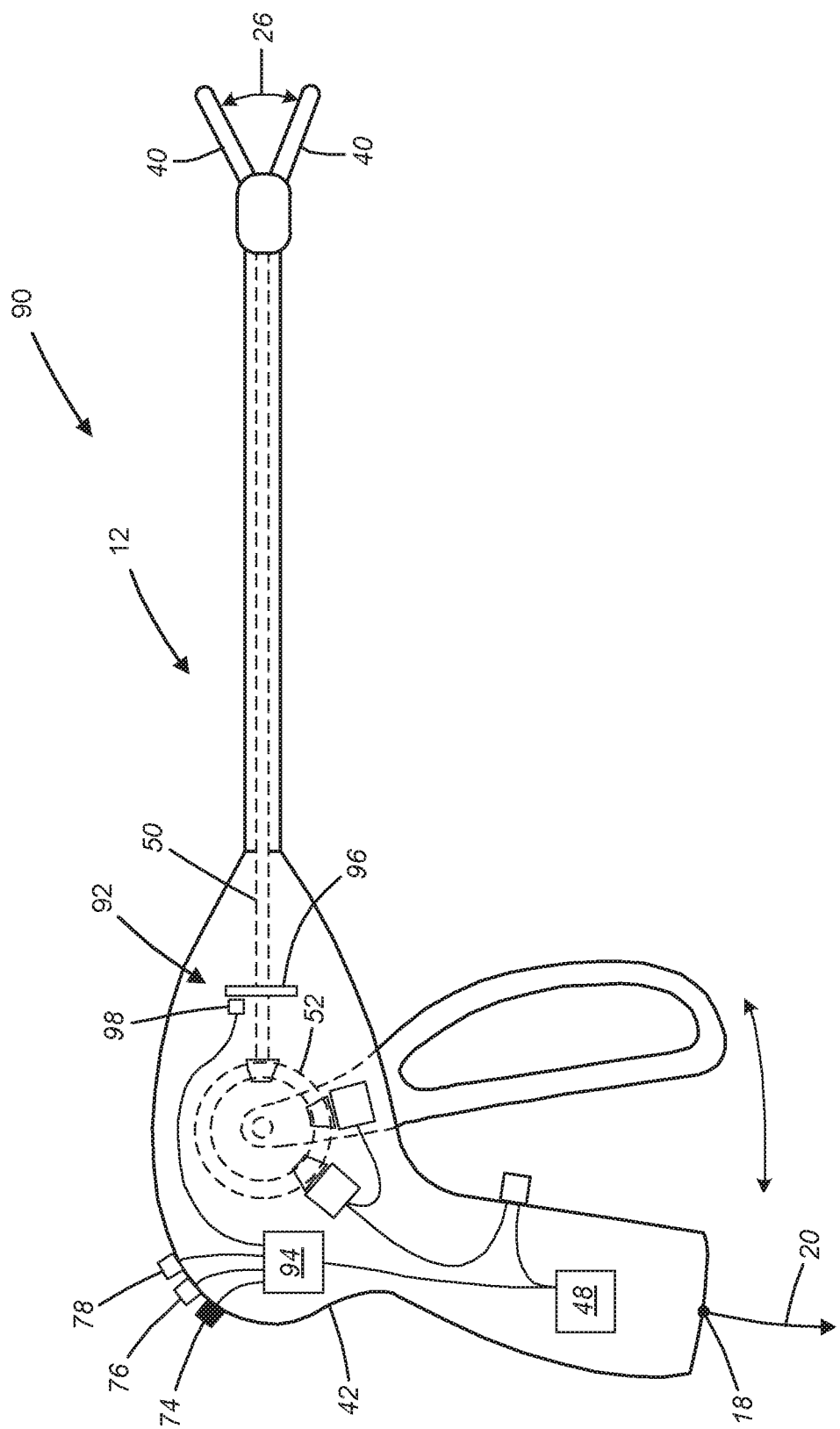
FIG. 8, FIG. 9, and FIG. 10 illustrate another hand held surgical instrument that is configured to provide feedback regarding whether jaw angle is suitable for tissue sealing and/or cutting, in accordance with some embodiments.
Figure 9:
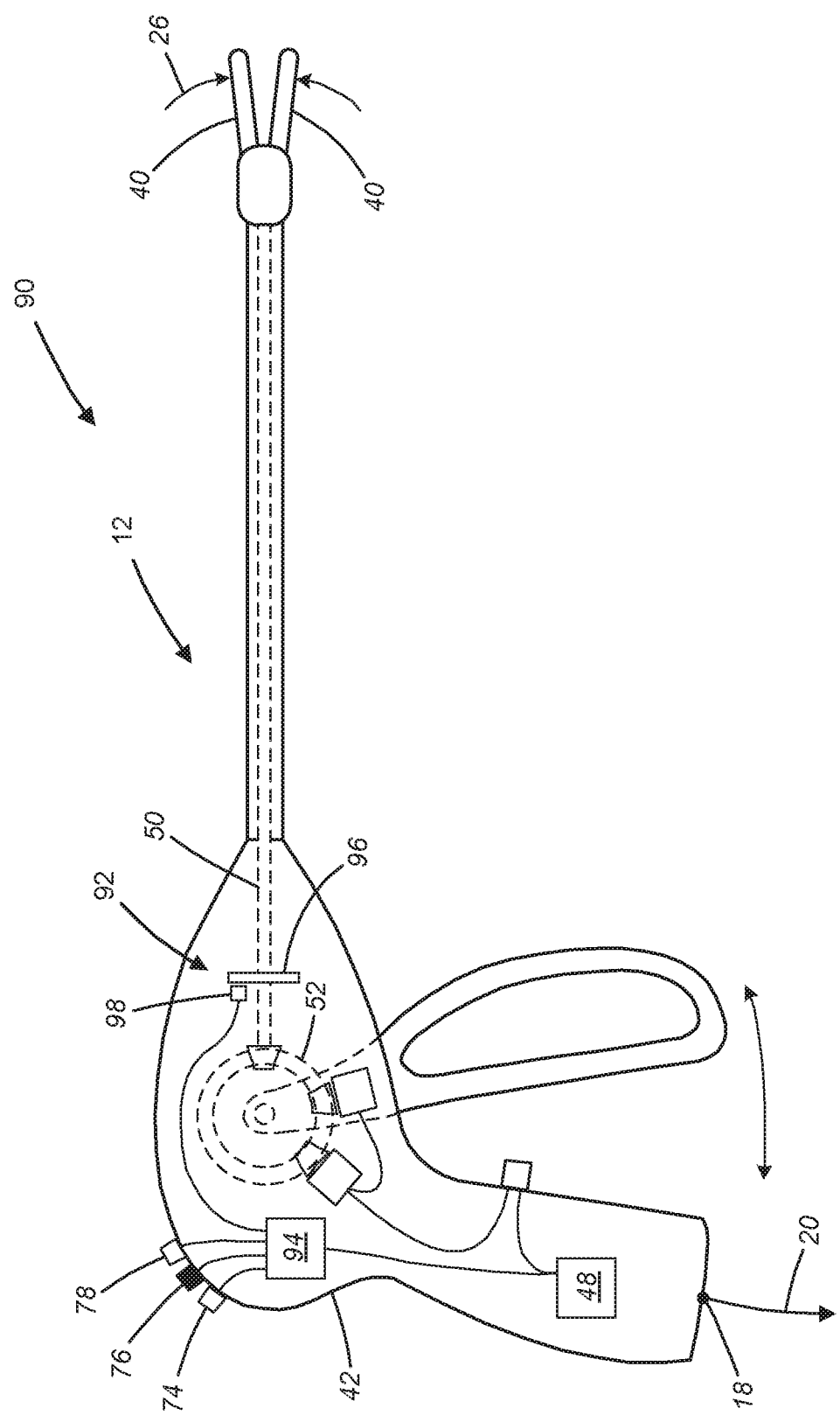
Figure 10:
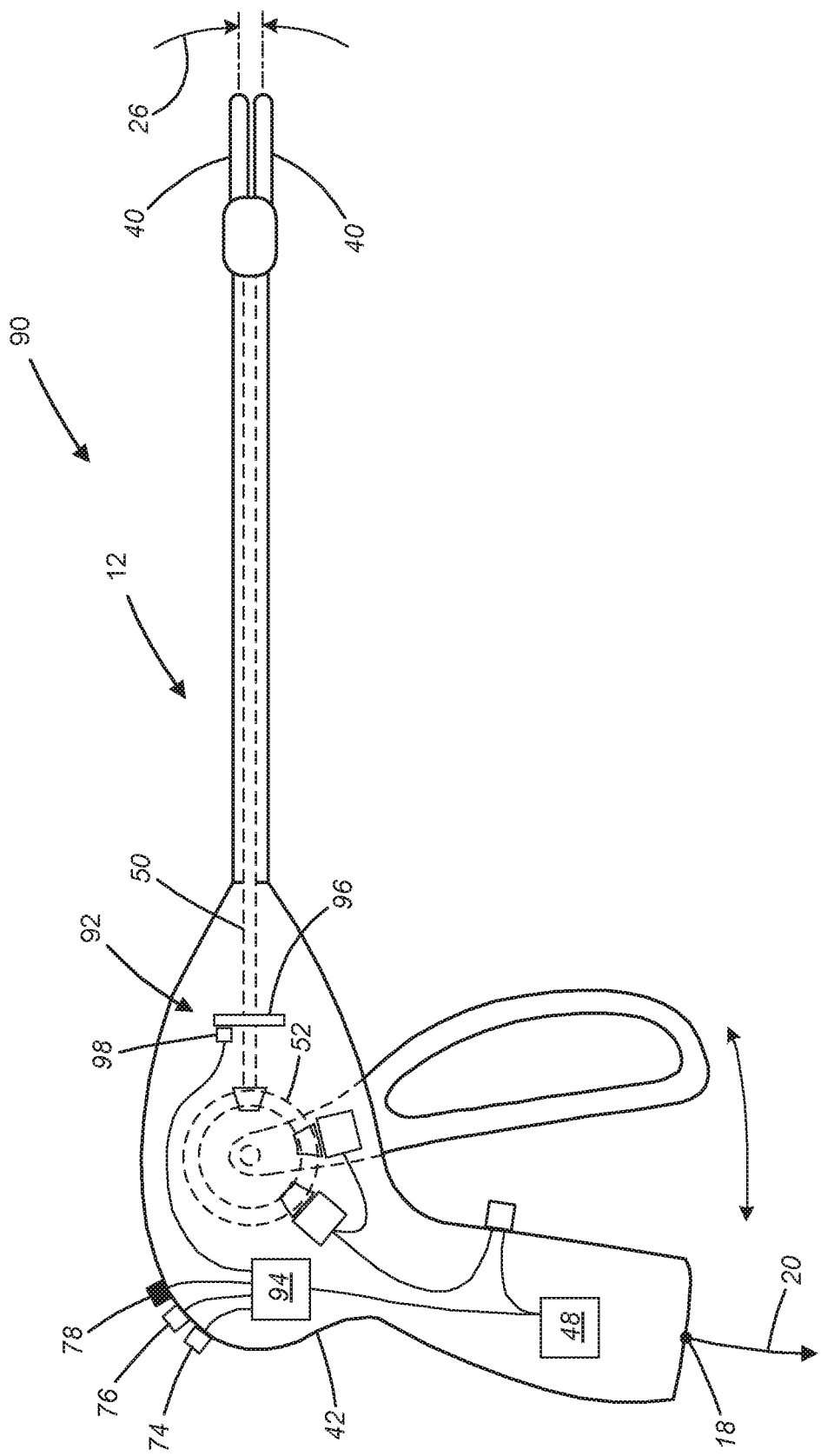

FIG. 8, FIG. 9, and FIG. 10 illustrate a hand held surgical instrument 90 that is configured to provide feedback regarding whether the current jaw angle 26 is suitable for tissue sealing and/or cutting, in accordance with some embodiments. The surgical instrument 90 includes the surgical instrument 12, an encoder assembly 92, and a control unit 94. The surgical instrument 90 can include one or more of feedback output lights 74, 76, 78 and/or the sealing enablement output 18. The encoder assembly 92 is configured to monitor the current jaw angle 26 of the jaws 40 by monitoring the angular orientation of the drive shaft 50. In the illustrated embodiment, the encoder assembly 92 includes an encoder disk 96 and an encoder sensor 98. The encoder disk 96 is attached to the drive shaft 50 to rotate with the drive shaft 50. The encoder sensor 98 is mounted to the housing 42 and generates an output signal indicative of changes in angular orientation of the encoder disk 96. The control unit 94 is operatively coupled with the encoder sensor 98 and the battery 48. The control unit 94 can be operatively coupled with one or more of the feedback output lights 74, 76, 78 and/or the sealing enablement output 18. The control unit 94 processes the output signal from the encoder sensor 98 to monitor the current jaw angle 26 and control lighting of the feedback output lights 74, 76, 78 in accordance with the current jaw angle 26 similar to as described herein with respect to the surgical instrument 70. As illustrated in FIG. 6, when the current jaw angle 26 of the jaws 40 is greater than the maximum recommended angle for sealing tissue clamped by the jaws 40 and greater than the maximum recommended angle for cutting tissue clamped by the jaws 40, the control unit 94 can energizes the output light 74. As illustrated in FIG. 7, when the current jaw angle 26 of the jaws 40 is equal to or less than the maximum recommended angle for sealing tissue clamped by the jaws 40 and greater than the maximum recommended angle for cutting tissue clamped by the jaws 40, the control unit 94 energizes the output light 76. As illustrated in FIG. 8, when the current jaw angle 26 of the jaws 40 is less than the maximum recommended angle for sealing tissue clamped by the jaws 40 and equal to or less than the maximum recommended angle for cutting tissue clamped by the jaws 40, the control unit 94 energizes the output light 78.

The surgical instrument 90 can be configured to include the sealing enablement output 18 and output the sealing enablement signal 20. With the surgical instrument 90, the sealing enablement signal 20 can be indicative of at least one of: (a) the current jaw angle 26 is greater than the maximum recommended clamping angle for sealing tissue clamped by the jaws 40, or (b) the current jaw angle 26 is equal to or less than the maximum recommended clamping angle for sealing tissue clamped by the jaws 40. When configured to include the sealing enablement output 18, the surgical instrument 90 can be used in the tissue sealing and cutting system 10 in lieu of the surgical instrument 12.

Figure 11:
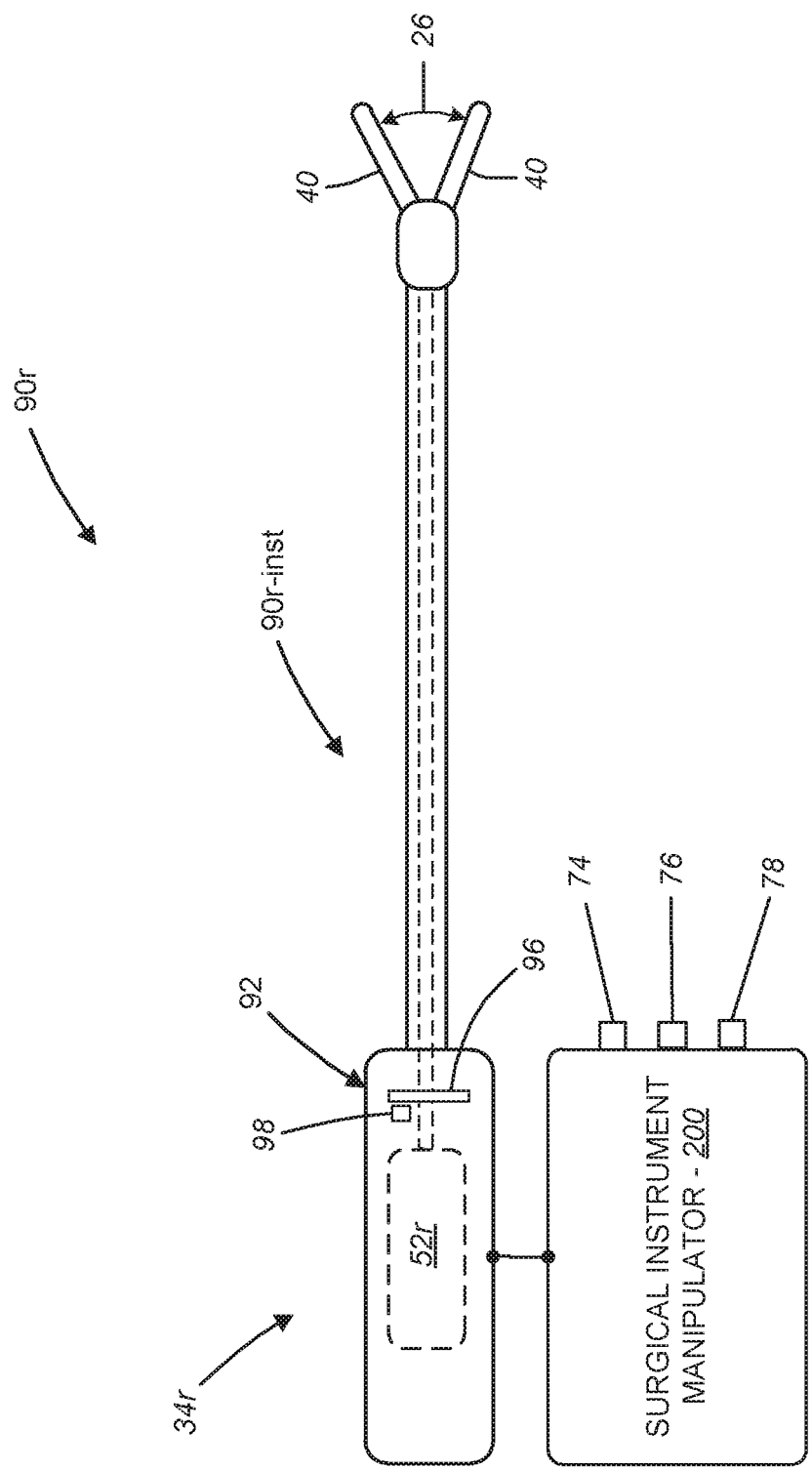
FIG. 11 illustrates a surgical assembly that is configured to provide feedback regarding whether jaw angle is suitable for tissue sealing and/or cutting, in accordance with some embodiments.

FIG. 11 illustrates a surgical assembly 90r for tissue sealing and/or cutting, in accordance with some embodiments. The surgical assembly 90r is configured similar to the surgical instrument 90, but includes a surgical instrument 90r-inst and the manipulator 200 to which the surgical instrument 90r-inst is detachably mountable for manipulation by an operator of the surgical assembly 90r. The surgical assembly 90r includes components similar to components of the surgical instruments 90 with the similar components being designated by the same or similar reference numbers and the description of such components of the surgical instrument 90 being applicable to the respective components of the surgical assembly 90r.

Figure 12:
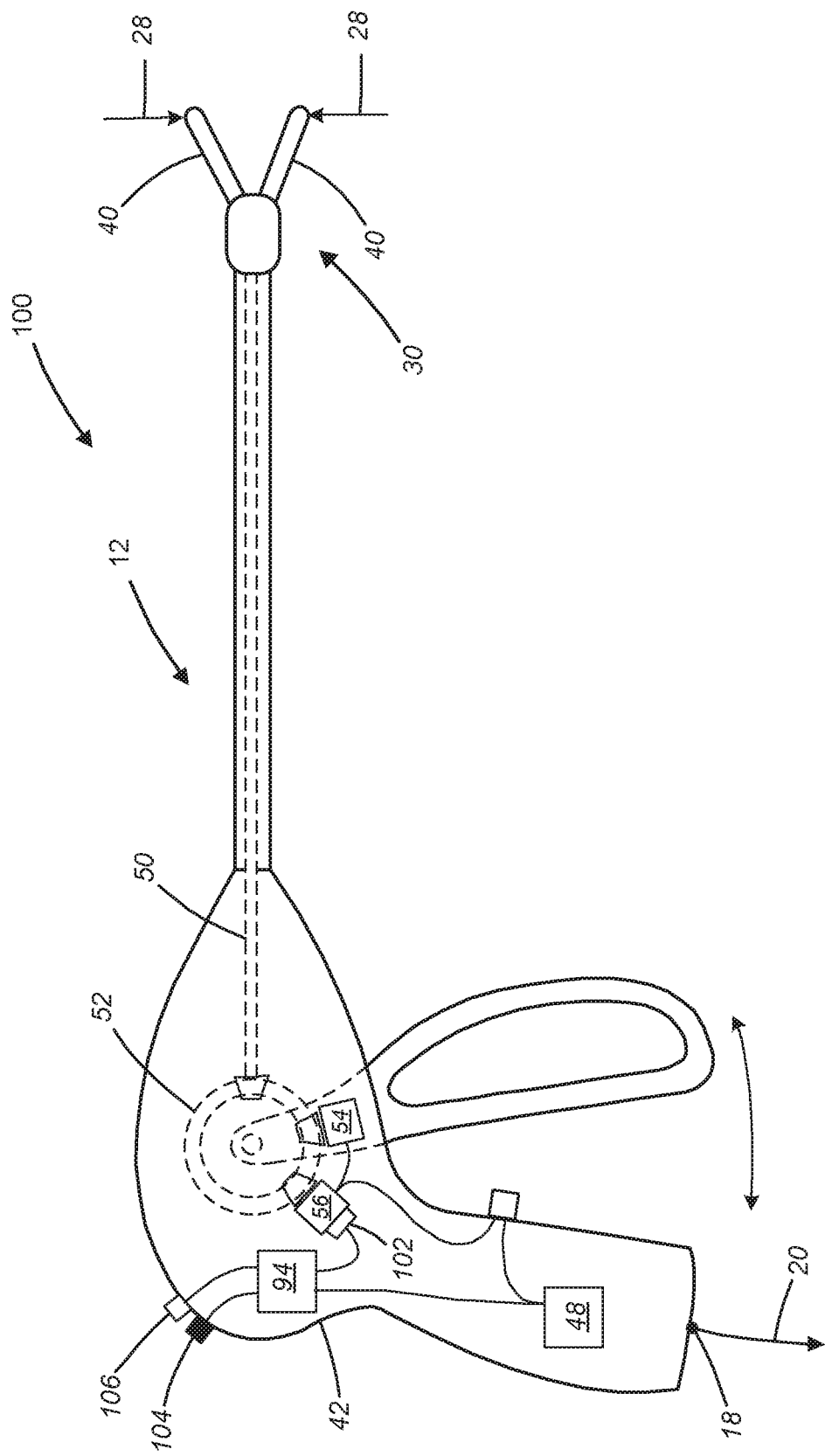
FIG. 12 and FIG. 13 illustrate a hand held surgical instrument that is configured to provide feedback regarding whether jaw clamping force is suitable for tissue sealing, in accordance with some embodiments.
Figure 13:
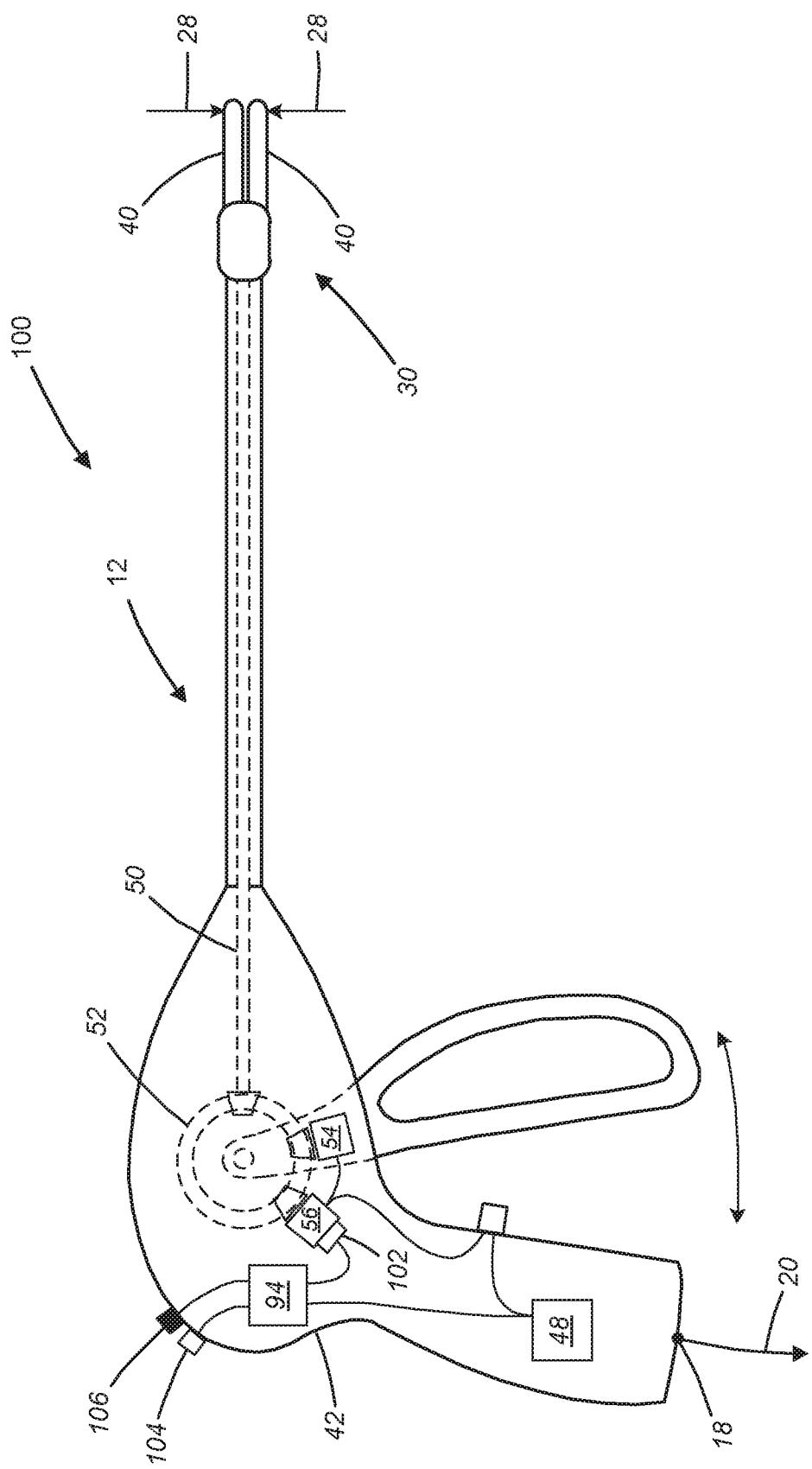

FIG. 12 and FIG. 13 illustrate a hand held surgical instrument 100 that is configured to provide feedback regarding whether the clamping force 28 of the jaws 40 is suitable for sealing tissue clamped by the jaws 40, in accordance with some embodiments. The surgical instrument 100 includes the surgical instrument 12, the control unit 94, and a torque sensor 102. The surgical instrument 100 can include one or more of feedback output lights 104, 106 and/or the sealing enablement output 18. The torque sensor 102 is configured to monitor torque transmitted via the drive shaft 50 to the end effector 30 and thereby monitor the clamping force 28 applied via the jaws 40 to tissue clamped by the jaws 40. In the illustrated embodiment, the torque sensor 102 is mounted to the housing 42 and supports the detent ratchet mechanism 56 so as to react torque transmitted into the detent ratchet mechanism 56 from the main gear 52 to the housing 42. The torque sensor 102 generates an output signal indicative of torque reacted by the torque sensor 102 into the housing 42. The control unit 94 processes the output signal from the torque sensor 102 to monitor the current clamping force 28. The surgical instrument 100 can includes feedback output lights 104, 106 that are used to feedback information to the operator of the surgical instrument 100 regarding whether the current clamping force 104 is suitable or unsuitable for sealing tissue clamped by the jaws 40. As illustrated in FIG. 9, when the current clamping force 28 applied to the tissue clamped by the jaws 40 is less than a minimum recommended clamping force for sealing tissue clamped by the jaws 40, the control unit 94 can energizes the output light 104. As illustrated in FIG. 10, when the current clamping force 28 of the jaws 40 is equal to or greater than the minimum recommended clamping force for sealing tissue clamped by the jaws 40, the control unit 94 energizes the output light 106.

The surgical instrument 100 can be configured to include the sealing enablement output 18 and output the sealing enablement signal 20. With the surgical instrument 100, the sealing enablement signal 20 can be indicative of at least one of: (a) the current clamping force 28 is less than the minimum recommended clamping force for sealing tissue clamped by the jaws 40, or (b) the current clamping force 28 is equal to or greater than the minimum recommended clamping force for sealing tissue clamped by the jaws 40. When configured to include the sealing enablement output 18, the surgical instrument 100 can be used in the tissue sealing and cutting system 10 in lieu of the surgical instrument 12.

Figure 14:
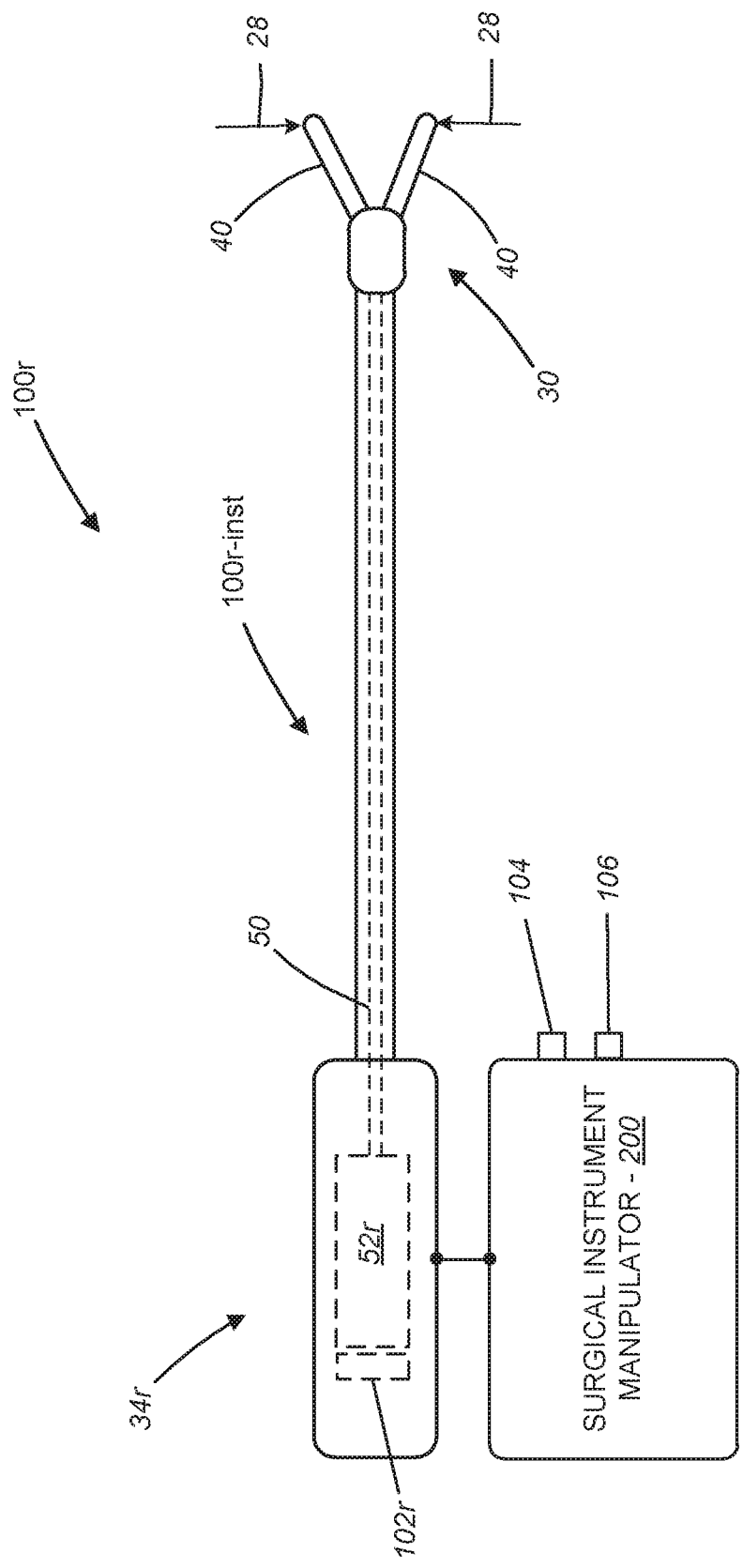
FIG. 14 illustrates a surgical assembly that is configured to provide feedback regarding whether jaw clamping force is suitable for tissue sealing, in accordance with some embodiments.

FIG. 14 illustrates a surgical assembly 100r for tissue sealing and/or cutting, in accordance with some embodiments. The surgical assembly 100r is configured similar to the surgical instrument 100, but includes a surgical instrument 100r-inst and the manipulator 200 to which the surgical instrument 100r-inst is detachably mountable for manipulation by an operator of the surgical assembly 100r. The surgical assembly 100r includes components similar to components of the surgical instrument 100 with the similar components being designated by the same or similar reference numbers and the description of such components of the surgical instrument 100 being applicable to the respective components of the surgical assembly 100r. The surgical assembly 100r includes a torque sensor 102r that is configured to monitor torque transmitted via the drive shaft 50 to the end effector 30 and thereby monitor the clamping force 28 applied via the jaws 40 to tissue clamped by the jaws 40. The surgical assembly 100r includes the feedback output lights 104, 106 that are used to feedback information to the operator of the surgical assembly 100r regarding whether the current clamping force 28 is suitable or unsuitable for sealing tissue clamped by the jaws 40 as described herein with respect to the surgical instrument 100.

Figure 15:
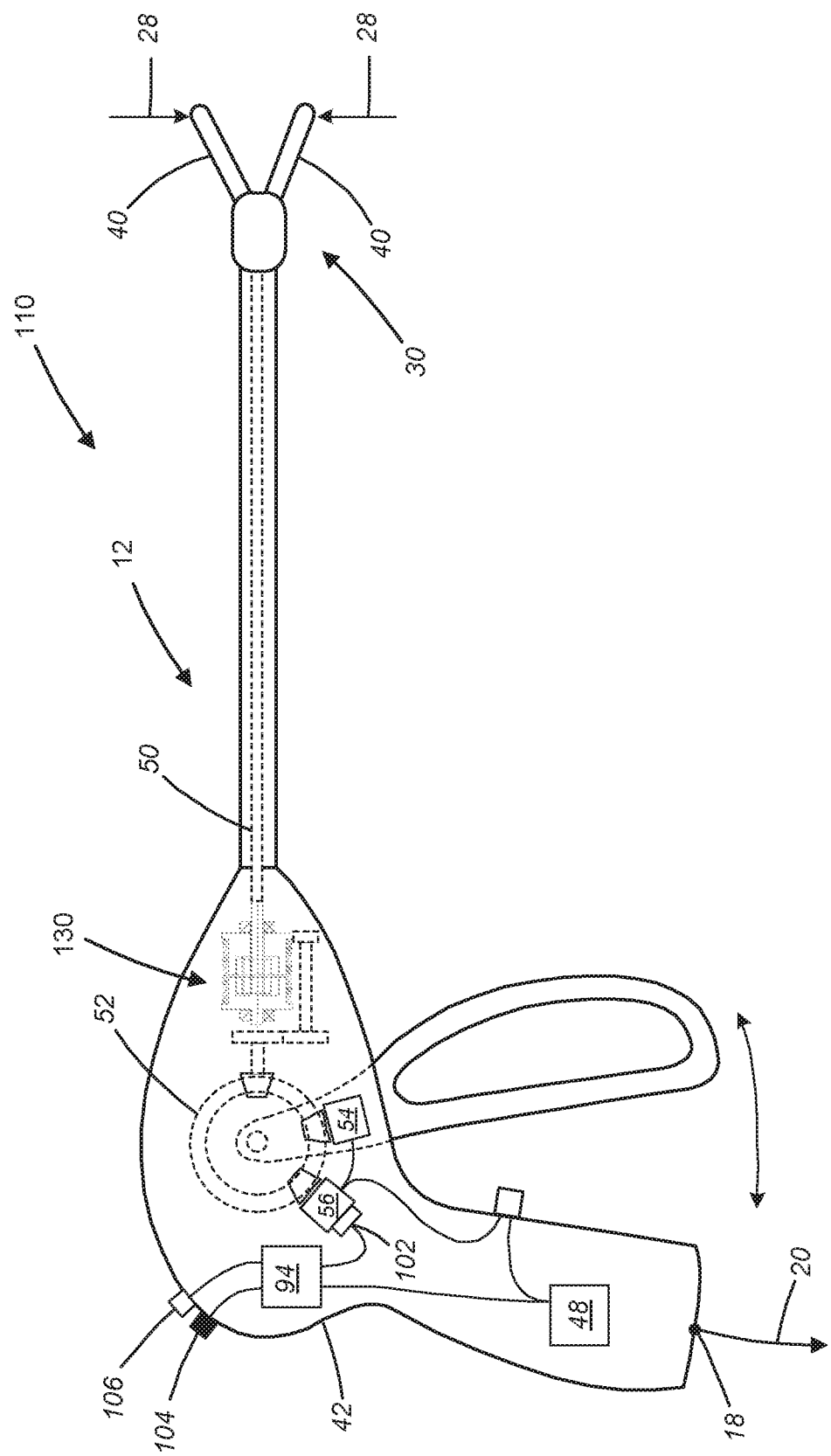
FIG. 15 and FIG. 16 illustrate a hand held surgical instrument that is configured to provide feedback regarding whether jaw clamping force is suitable for tissue sealing and/or cutting and includes a spring assembly configured to control jaw clamping force, in accordance with some embodiments.
Figure 16:
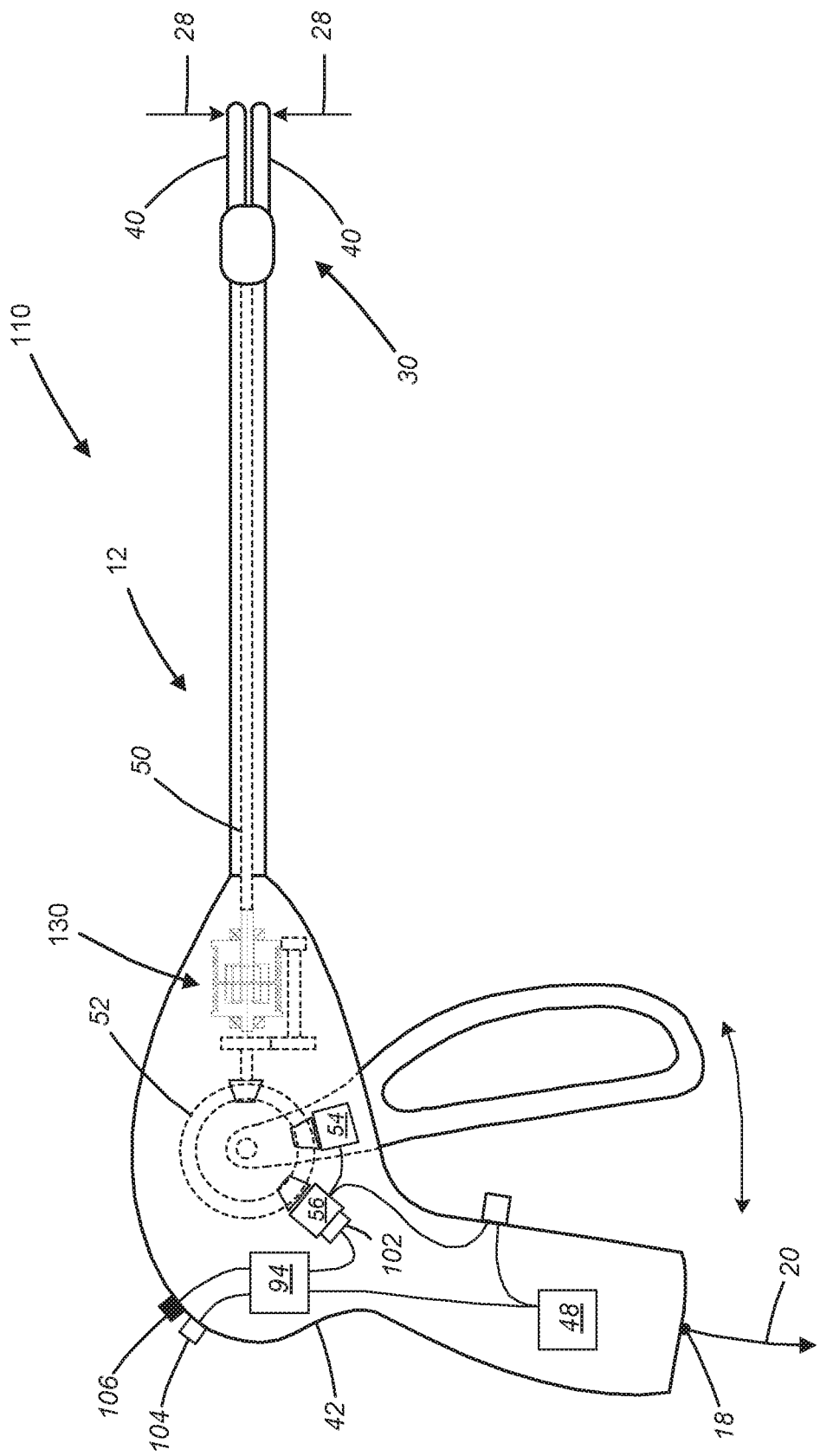

FIG. 15 and FIG. 16 illustrate a hand held surgical instrument 110 that includes a torsion spring assembly 130 configured to control the jaw clamping force 28. The surgical instrument 110 is configured to provide feedback regarding whether the jaw clamping force 28 is suitable for sealing tissue clamped by the jaws 40, in accordance with some embodiments. The surgical instrument 110 includes a modified version of the surgical instrument 12 that incorporates the torsion spring assembly 130, the control unit 94, and the torque sensor 102. The surgical instrument 110 can include one or more of feedback output lights 104, 106 and/or the sealing enablement output 18.

The torsion spring assembly 130 is configured to control the amount of transmitted torque/force in one direction (e.g., in the direction corresponding to closing of the jaws 40. For torques/forces transmitted in the direction corresponding to opening of the end effector jaw, the direction of transmitted torques/forces further adds to the preloaded spring forces in preventing relative movement between the input link 132 and the output link 134. As illustrated in FIG. 15, when the current clamping force 28 applied to the tissue clamped by the jaws 40 is less than a minimum recommended clamping force for sealing tissue clamped by the jaws 40, the control unit 94 energizes the output light 104. As illustrated in FIG. 16, when the current clamping force 28 of the jaws 40 is equal to or greater than the minimum recommended clamping force for sealing tissue clamped by the jaws 40, the control unit 94 energizes the output light 106.

The surgical instrument 110 can be configured to include the sealing enablement output 18 and output the sealing enablement signal 20. With the surgical instrument 110, the sealing enablement signal 20 can be indicative of at least one of: (a) the current clamping force 28 is less than the minimum recommended clamping force for sealing tissue clamped by the jaws 40, or (b) the current clamping force 28 is equal to or greater than the minimum recommended clamping force for sealing tissue clamped by the jaws 40. When configured to include the sealing enablement output 18, the surgical instrument 110 can be used in the tissue sealing and cutting system 10 in lieu of the surgical instrument 12.

Figure 17:
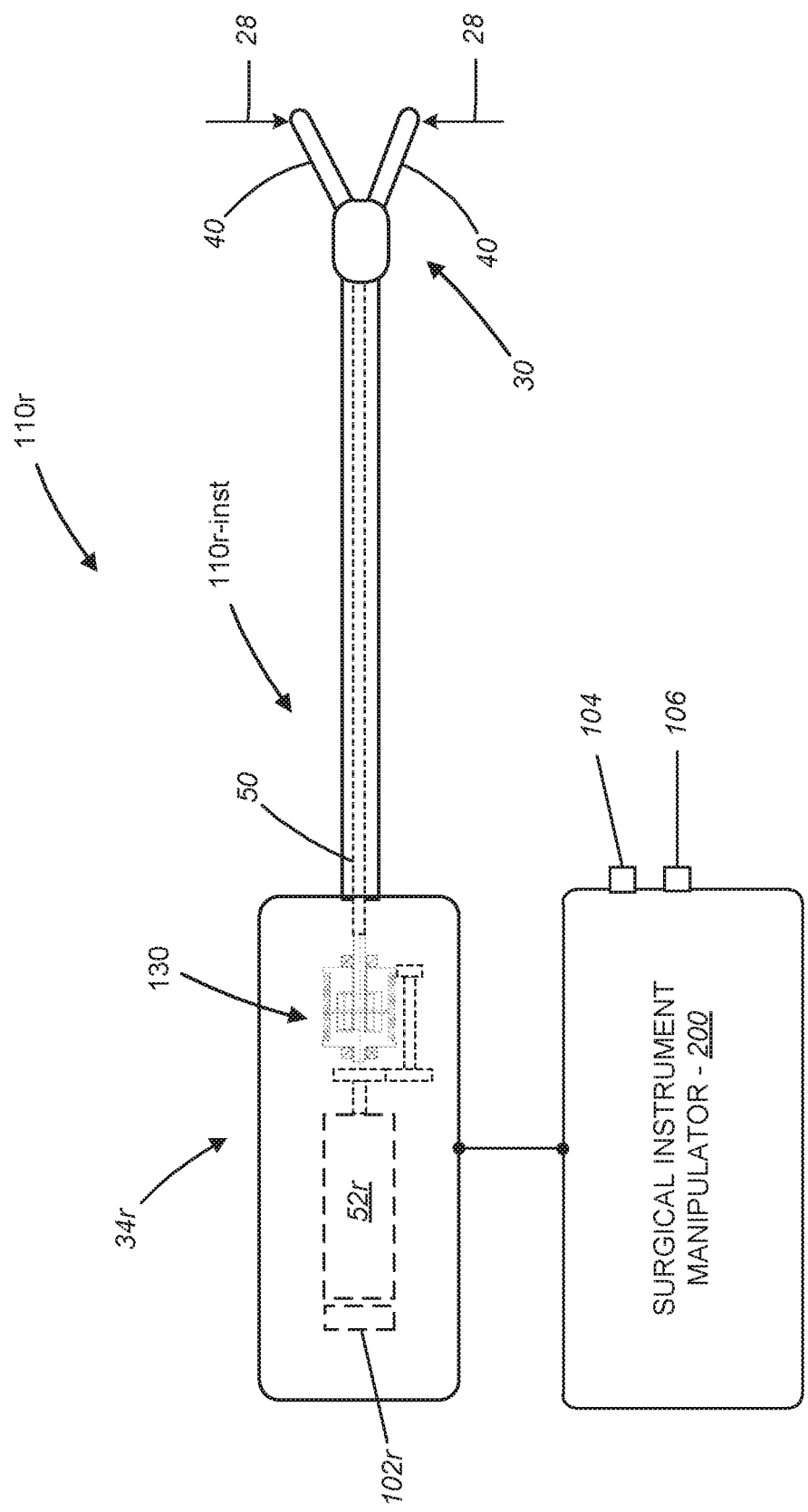
FIG. 17 illustrates a surgical assembly configured to provide feedback regarding whether jaw clamping force is suitable for tissue sealing and/or cutting and including a spring assembly configured to control jaw clamping force, in accordance with some embodiments.

FIG. 17 illustrates a surgical assembly 110r for tissue sealing and/or cutting, in accordance with some embodiments. The surgical assembly 110r is configured similar to the surgical instrument 110, but includes a surgical instrument 110r-inst and the manipulator 200 to which the surgical instrument 110r-inst is detachably mountable for manipulation by an operator via the manipulator 200. The surgical assembly 110r includes components similar to components of the surgical instrument 110 with the similar components being designated by the same or similar reference numbers and the description of such components of the surgical instrument 110 being applicable to the respective components of the surgical assembly 110r. The surgical assembly 110r includes the torsion spring assembly 130 and the feedback output lights 104, 106, which are used to feedback information to the operator of the surgical assembly 110r regarding whether the current clamping force 28 is suitable or unsuitable for sealing tissue clamped by the jaws 40 as described herein with respect to the surgical instrument 100.

Figure 18:
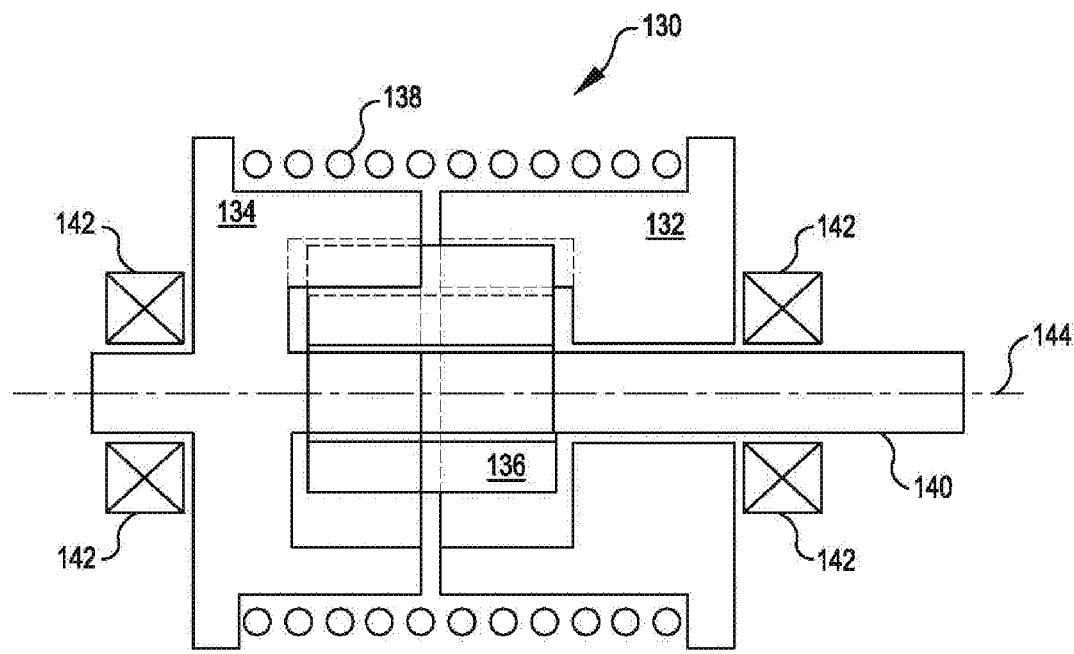
FIG. 18, FIG. 19, and FIG. 20 illustrate attributes of a spring assembly configured to control jaw clamping force, in accordance with some embodiments.

FIG. 18 schematically illustrates the torsion spring assembly 130, which is configured to control the amount of clamping force that is transmitted to jaws 40. The torsion spring assembly 130 includes an input link 132 that is rotationally coupled with the main gear 52, an output link 134 that is rotationally coupled with the drive shaft 50, an interface element 136, and a torsion spring 138 coupled between the input link 132 and the output link 134. The output link 134 is fixedly attached to (or integral with) a central shaft 140. The torsion spring assembly 130 is rotationally mounted to the housing 42 via shaft bearings 142. The input link 132 and the interface element 136 are mounted to rotate about a central axis 144 of the central shaft 140. The torsion spring 138 coupled between the input link 132 and the output link 134 is in a preloaded state.

Figure 19:
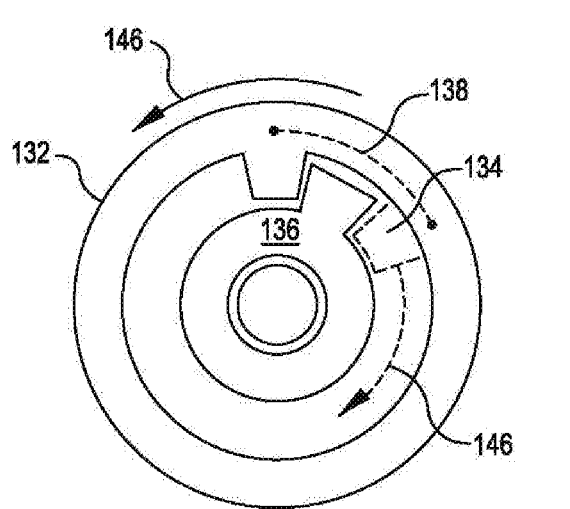
Figure 20:
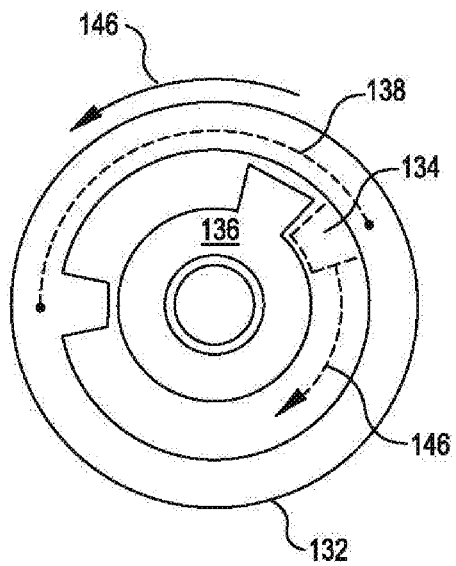

In operation the torsion spring assembly 130 transmits torque from the input link 132 to the output link 134. Referring to FIG. 19, when the transmitted torque 146 is below a predetermined level (i.e., the torsion preload in the torsion spring 138), the level of preload in the torsion spring 138 is sufficient to bias the output link 134 into contact with the interface element 136, which in turn is biased into contact with the input link 132. Referring to FIG. 20, when the transmitted torque 146 exceeds the predetermined level, the level of preload in the torsion spring 138 is insufficient to maintain the contact between the output link 134, the interface element 136, and the input link 132, and as a result additional rotational deformation of the torsion spring 138 occurs. When the transmitted torque 146 exceeds the predetermined level, the torque transmitted through the torsion spring assembly 130 is transmitted through the torsion spring 138.

The interface element 136 serves a number of purposes. Contact between the interface element 136 and the input and output links 132, 134 maintains a relative angular orientation between the input link 132 and the output link 134 for torques transmitted through the torsion spring assembly 130 that are less than the predetermined level. The interface element 136 also serves to increase the amount of possible angular deflection that can occur between the input link 132 and the output link 134 for torques transmitted through the torsion spring assembly 130 that exceed the predetermined level. The torsion spring assembly 130 can be configured without the interface element 136 by configuring the input and output links 132, 134 with features that provide for direct contact between input and output links analogous to the contact provided by the interface element 136 (e.g., the interface element 136 could be made integral to the input link 132, or the interface element 136 could be made integral to the output link 134). In such embodiments without the interface element 136, the amount of possible angular deflection that can occur between the input link 132 and the output link 134 may be limited to something slightly less than 360 degrees (e.g., approximately 345 degrees). With an interface element 136, which can rotate about the central axis 144, the amount of possible angular deflection that can occur between the input link 132 and the output link 134 may be greater (e.g., approximately 690 degrees). Any suitable number of interface elements 136 (e.g., 0, 1, 2, 3 or more, etc.) can be used suitable for the amount of possible angular deflection desired between the input link 132 and the output link 134.

Figure 21:
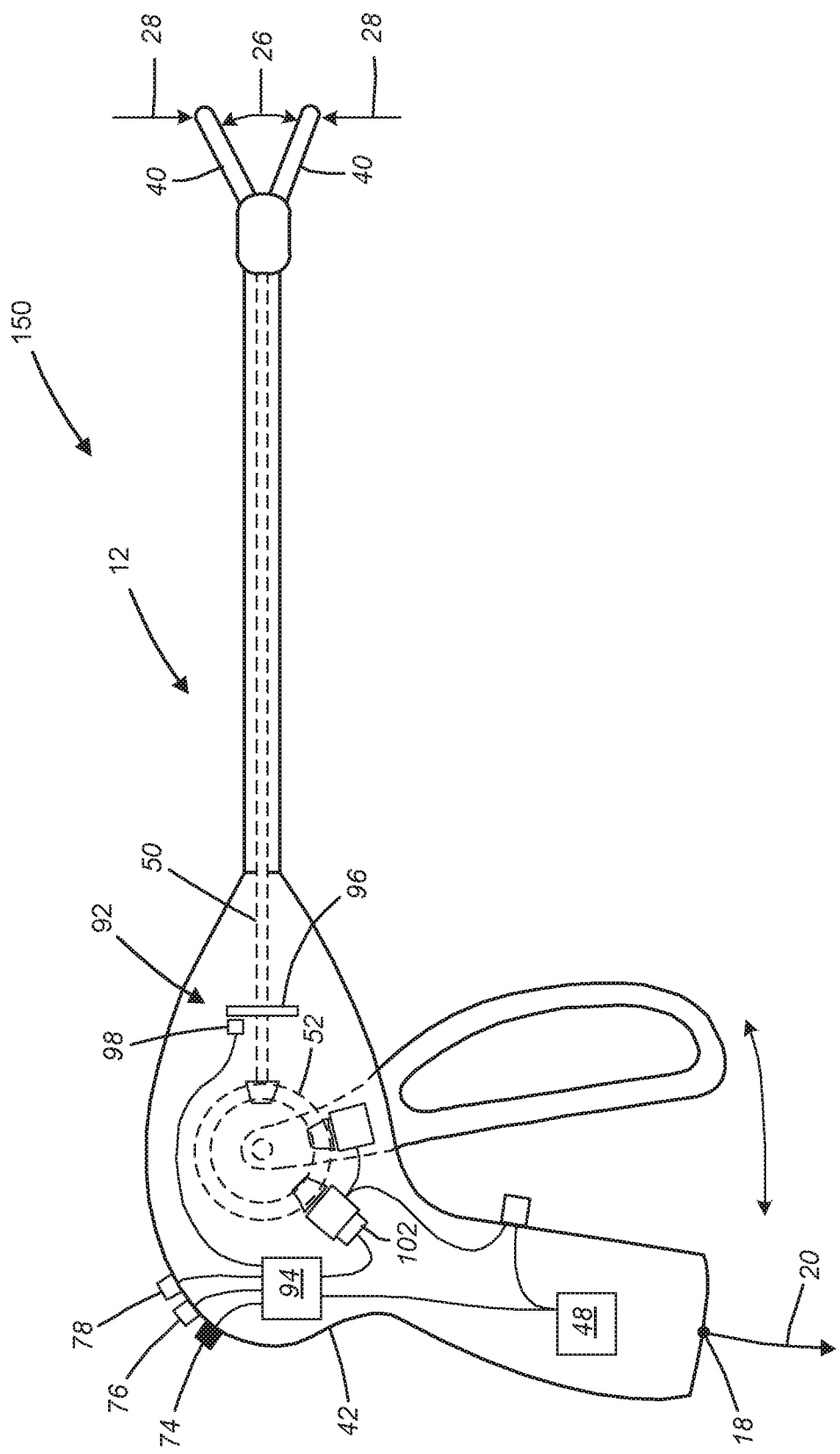
FIG. 21, FIG. 22, and FIG. 23 illustrate a hand held surgical instrument that is configured to monitor jaw angle and jaw clamping force and to provide feedback based on the jaw angle and jaw clamping force regarding whether the jaw angle and/or jaw clamping force is suitable for tissue sealing and/or cutting, in accordance with some embodiments.
Figure 22:
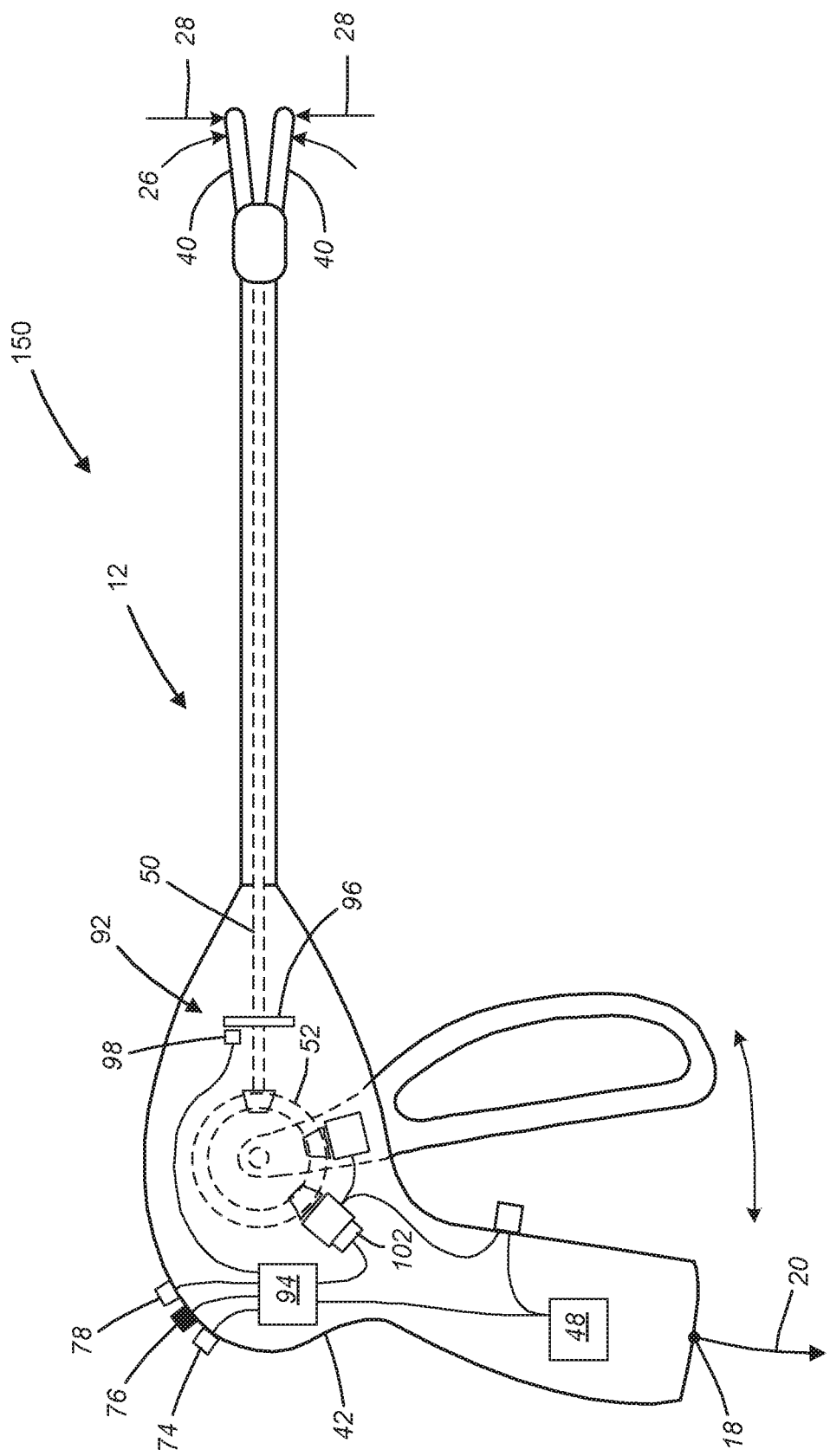
Figure 23:
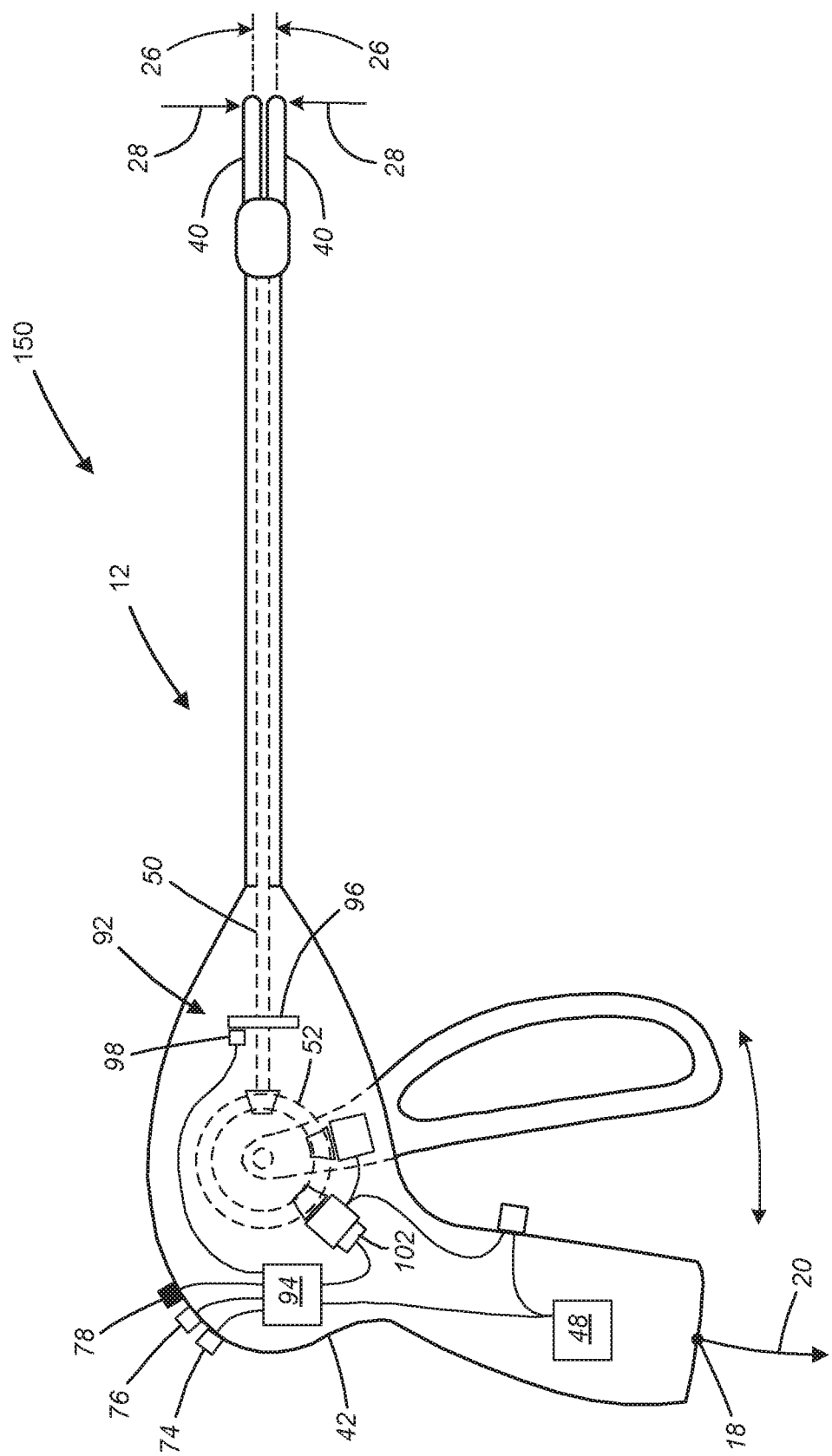

FIG. 21, FIG. 22, and FIG. 23 illustrate a hand held surgical instrument 150 that is configured to monitor the current jaw angle 26 and the current clamping force 28 of the jaws 40 and to provide feedback based on the current jaw angle 26 and the current clamping force 28 regarding whether the current jaw angle 26 and/or the current clamping force 28 is suitable for sealing and/or cutting tissue clamped by the jaws 40, in accordance with some embodiments. The surgical instrument 150 includes the surgical instrument 12, the control unit 94, the torque sensor 102, and the encoder assembly 92. The surgical instrument 150 can include one or more of feedback output lights 74, 76, 78 and/or the sealing enablement output 18.

In the surgical instrument 150, the control unit 94 processes output from the encoder assembly 92 to monitor the current jaw angle 26 of the jaws 40 and processes output from the torque sensor 102 to monitor the current clamping force 28 of the jaws 40. Based on the current jaw angle 26 and the current clamping force 28, the control unit 94 can be configured to provide feedback to the operator of the surgical instrument 150 via the feedback output lights 74, 76, 78. As illustrated in FIG. 21, when the current jaw angle 26 and the current clamping force 28 are not suitable for sealing tissue clamped by the jaws 40, the control unit 94 energizes the output light 74. For example, the control unit 94 can be configured to energize the output light 74 if the current jaw angle 26 is greater than a maximum recommended angle for sealing tissue or if the current clamping force 28 is less than a minimum recommended clamping force for sealing tissue. In some embodiments, the control unit 94 energizes the output light 74 based only on the current clamping force 28 thereby providing feedback to the operator of the surgical instrument 150 that the current clamping force 28 is less than a minimum recommended clamping force for sealing tissue. As illustrated in FIG. 22, when the current jaw angle 26 and the current clamping force 28 are suitable for sealing tissue clamped by the jaws 40 and the current jaw angle 26 is greater than a maximum recommended angle for cutting tissue, the control unit 94 energizes the output light 76. For example, the control unit 94 can be configured to energize the output light 76 if the current jaw angle 26 is equal to or less than a maximum recommended angle for sealing tissue, the current clamping force 28 is equal to or greater than a minimum recommended clamping force for sealing tissue, and the current jaw angle 26 is greater than a maximum recommended angle for cutting tissue. In some embodiments, the control unit 94 energizes the output light 76 when the current clamping force 28 is greater than a minimum recommended clamping force for sealing tissue and the current jaw angle 26 is greater than a maximum recommended angle for cutting tissue, thereby providing corresponding feedback to the operator of the surgical instrument 150. As illustrated in FIG. 23, when the current jaw angle 26 and the current clamping force 28 are suitable for sealing tissue clamped by the jaws 40 and the current jaw angle 26 is equal to or less than a maximum recommended angle for cutting tissue, the control unit 94 energizes the output light 78. For example, the control unit 94 can be configured to energize the output light 78 if the current jaw angle 26 is equal to or less than a maximum recommended angle for sealing tissue, the current clamping force 28 is equal to or greater than a minimum recommended clamping force for sealing tissue, and the current jaw angle 26 is equal to or less than the maximum recommended angle for cutting tissue.

The surgical instrument 150 can be configured to include the sealing enablement output 18 and output the sealing enablement signal 20. With the surgical instrument 150, the sealing enablement signal 20 can be indicative of at least one of: (a) the current jaw angle 26 is greater than the maximum recommended clamping angle for sealing tissue clamped by the jaws 40 or the current clamping force 28 is less than the minimum recommended clamping force for sealing tissue clamped by the jaws 40, or (b) the current jaw angle 26 is equal to or less than the maximum recommended clamping angle for sealing tissue clamped by the jaws 40 and the current clamping force 28 is equal to or greater than the minimum recommended clamping force for sealing tissue clamped by the jaws 40. When configured to include the sealing enablement output 18, the surgical instrument 150 can be used in the tissue sealing and cutting system 10 in lieu of the surgical instrument 12.

Figure 24:
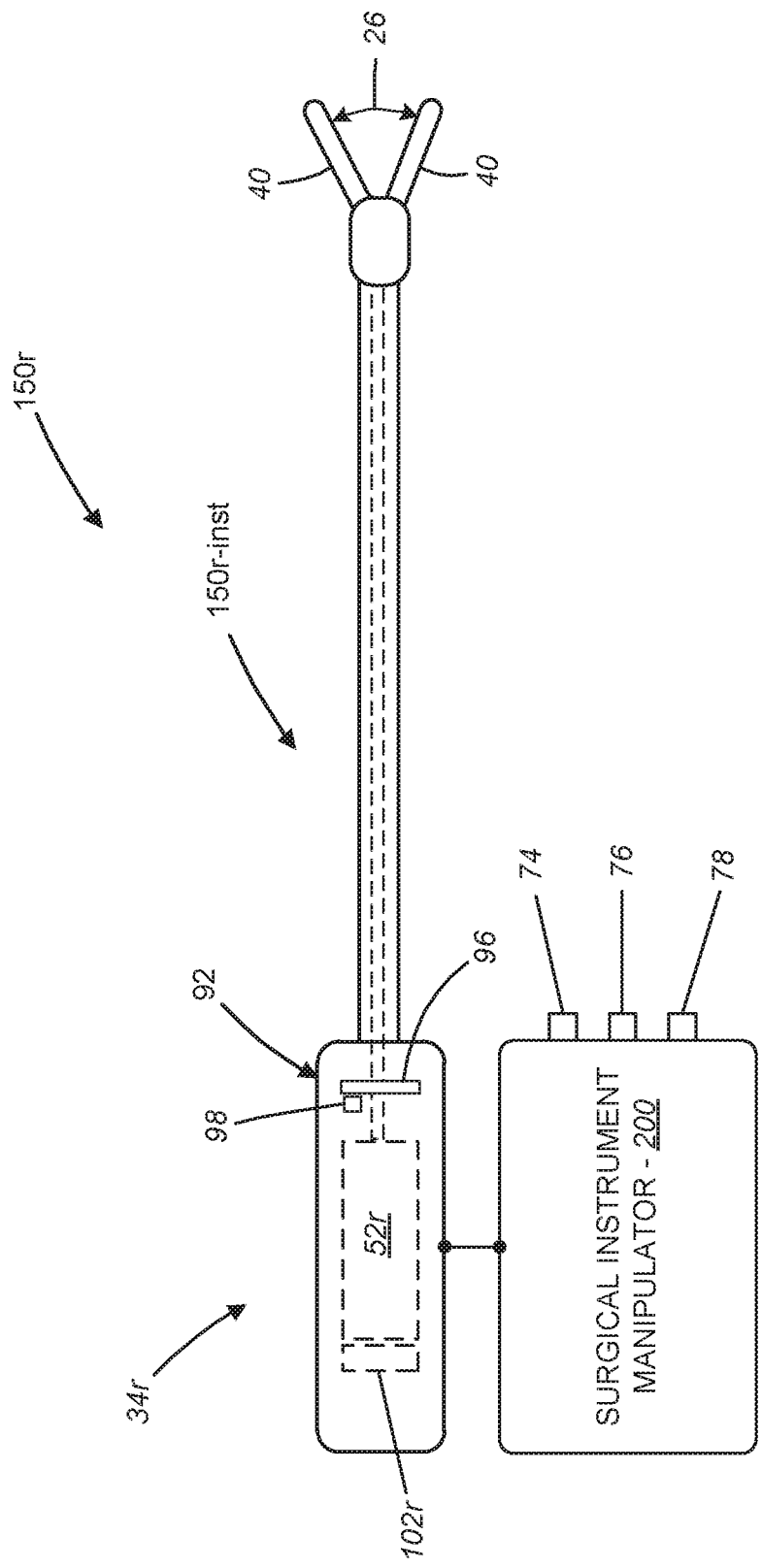
FIG. 24 illustrates a surgical assembly configured to monitor jaw angle and jaw clamping force and to provide feedback based on the jaw angle and jaw clamping force regarding whether the jaw angle and/or jaw clamping force is suitable for tissue sealing and/or cutting, in accordance with some embodiments.

FIG. 24 illustrates a surgical assembly 150r for tissue sealing and/or cutting, in accordance with some embodiments. The surgical assembly 150r is configured similar to the surgical instrument 150, but includes a surgical instrument 150r-inst and the manipulator 200 to which the surgical instrument 150r-inst is detachably mountable for manipulation by an operator via the manipulator 200. The surgical assembly 150r includes components similar to components of the surgical instrument 150 with the similar components being designated by the same or similar reference numbers and the description of such components of the surgical instrument 150 being applicable to the respective components of the surgical assembly 150r. For example, surgical assembly 150r includes the encoder assembly 92, a torque sensor 102r (which is configured similar to the torque sensor 102), and output lights 74, 76, 78. In some embodiments, the surgical assembly 150r includes a control unit that processes output from the encoder assembly 92 to monitor the current jaw angle 26 of the jaws 40 and processes output from the torque sensor 102r to monitor the current clamping force 28 of the jaws 40. Based on the current jaw angle 26 and the current clamping force 28, the control unit is configured to provide feedback to the operator of the surgical assembly 150r via the feedback output lights 74, 76, 78 as described herein with regard to the surgical instrument 150.

Figure 25:
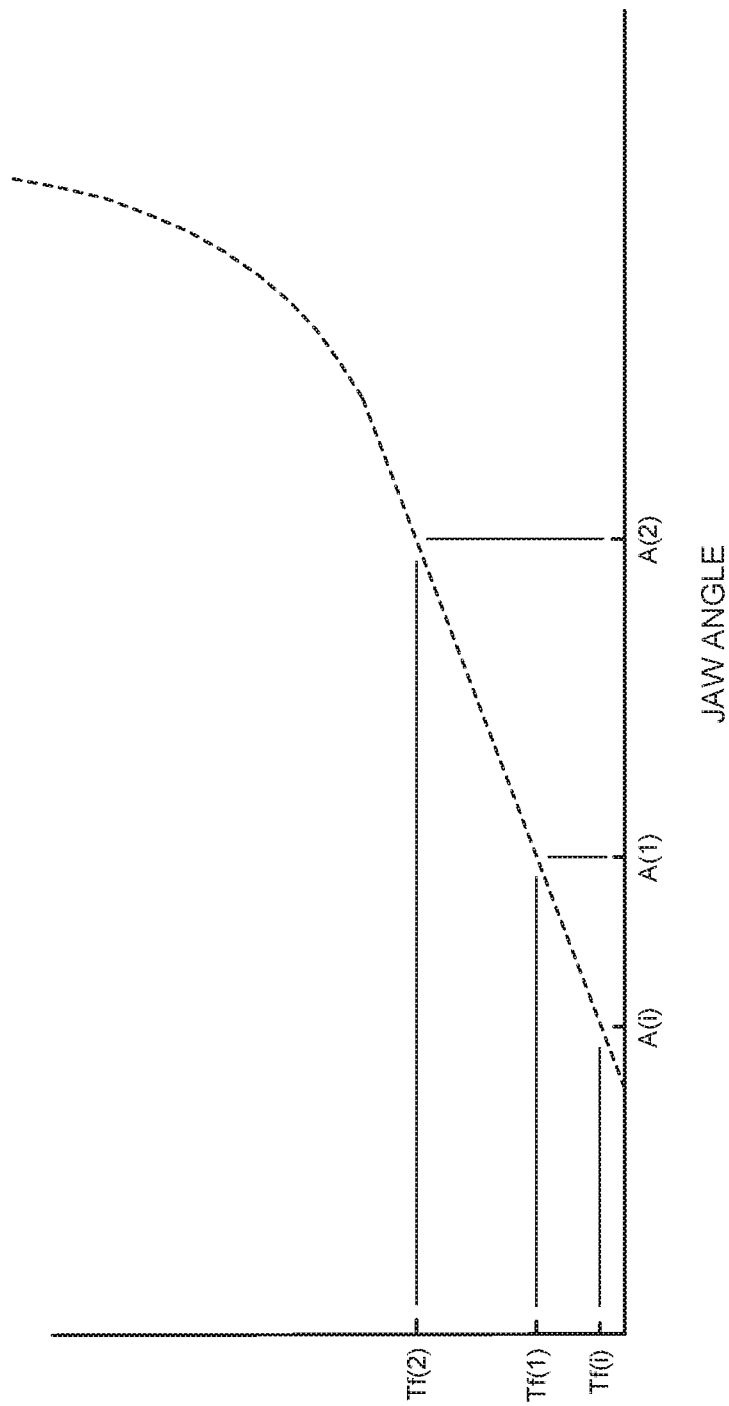
FIG. 25 illustrates processing of jaw angle and clamping force to identify an initial contact jaw angle corresponding to initial contact between a jaw and tissue clamped by the jaw and to determine a tissue stiffness of tissue clamped by the jaw, in accordance with some embodiments.

FIG. 25 illustrates processing of the current jaw angle 26 and the current clamping force 28 that can be accomplished by the control unit 94 to identify an initial contact jaw angle (A(i)) corresponding to initial contact between an jaws 40 and tissue clamped by the jaws 40 and to determine a stiffness of tissue clamped by the jaws 40, in accordance with some embodiments. Any of the surgical instruments described herein that are configured to monitor both the current jaw angle 26 and the current clamping force 28 can implement the processing illustrated in FIG. 25. As the jaws 40 are articulated to close to clamp tissue, once the jaws 40 make contact with the tissue, the torque required to further close the jaws 40 increases. The control unit 94 can monitor the output of the torque sensor 102 to detect when the output of the torque sensor 102 indicates that the current clamping force 28 exceeds a suitable threshold (e.g., Tf(i)) to reliably identify the current jaw angle 26 corresponding to initial contact between the jaws 40 and tissue clamped by the jaws 40. The control unit 94 can continue to monitor the output of the torque sensor 102 and the current jaw angle 26 to identify jaw angles (A(1), A(2)) for respective outputs (Tf(1), Tf(2)) of the torque sensor 102 and use the jaw angles (A(1), A(2)) and the respective clamping forces 28 to calculate a stiffness for the tissue clamped by the jaws 40.

Figure 26:
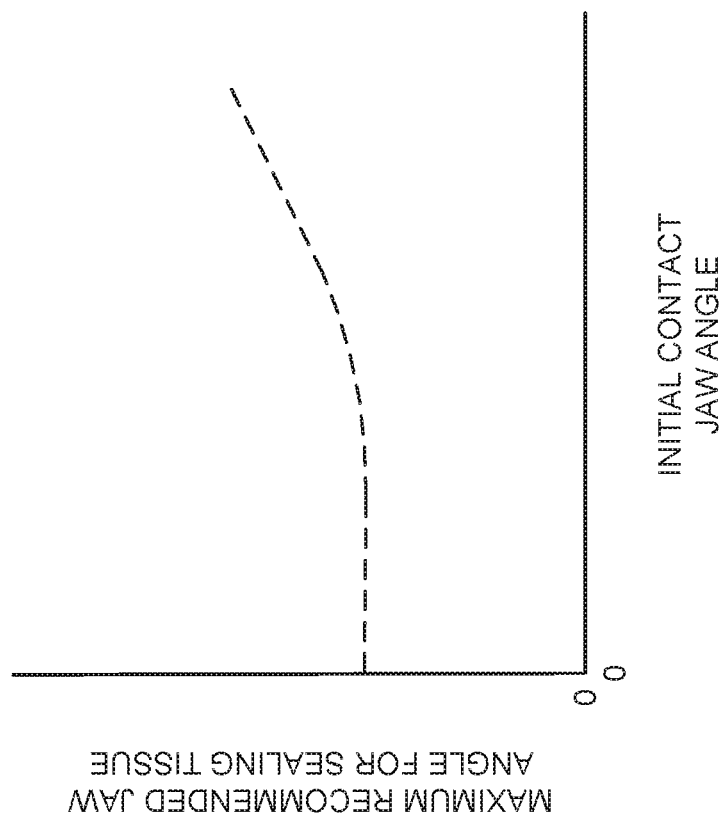
FIG. 26 shows an example variation of a maximum recommended jaw angle for sealing tissue for a range of initial contact jaw angles, in accordance with some embodiments.

The control unit 94 can be configured to vary the maximum recommended jaw angle based on the initial contact jaw angle. For example, FIG. 26 shows an example variation of a maximum recommended jaw angle for sealing tissue for a range of initial contact jaw angles, in accordance with some embodiments. As shown in FIG. 26, when the tissue is small, the initial contact jaw angle will be small and the maximum recommended jaw angle for sealing the tissue can be set to a suitable value for the small tissue. For increasingly larger tissues, the initial contact jaw angle will increase and a larger maximum recommended jaw angle may be suitable for sealing the larger tissue. The control unit 94 can access a suitable look-up table in memory to retrieve a suitable maximum recommended jaw angle from memory corresponding to the detected initial contact jaw angle. Any of the surgical instruments described herein that are configured to monitor both the current jaw angle 26 and the current clamping force 28 can implement the approach illustrated in FIG. 26.

Figure 27:
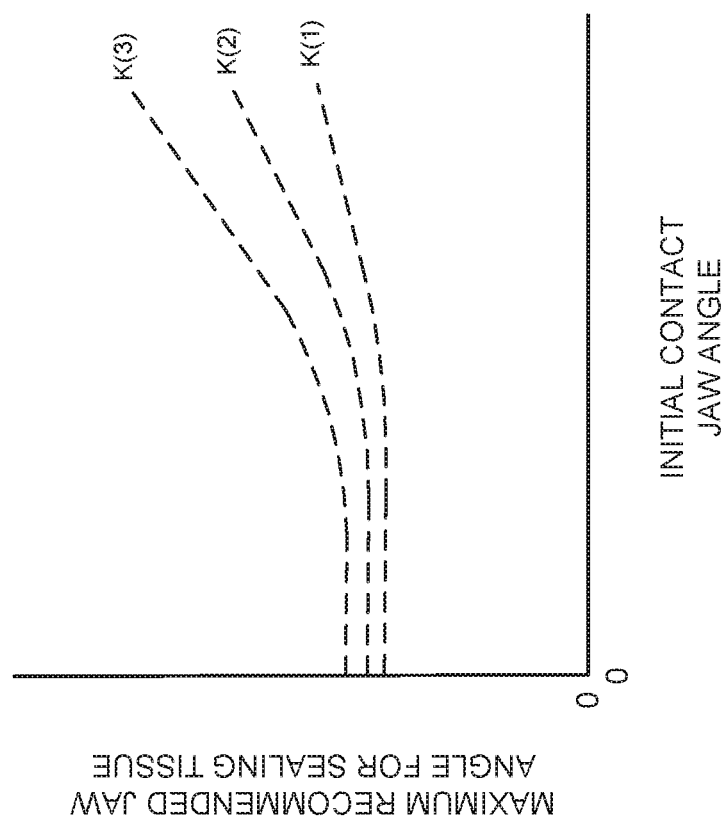
FIG. 27 shows example variations of a maximum recommended jaw angle for sealing tissue for a range of initial contact jaw angles and different tissue stiffnesses, in accordance with some embodiments.

The control unit 94 can be configured to vary the maximum recommended jaw angle based on the initial contact jaw angle and tissue stiffness. For example, FIG. 27 shows an example variation of a maximum recommended jaw angle for sealing tissue for a range of initial contact jaw angles and different tissue stiffness, in accordance with some embodiments. In addition to the variation of the maximum recommend jaw angles for sealing tissue based on initial contact jaw angle, FIG. 27 shows example variations due to different tissue stiffness (K(1), K(2), K(3)). For different tissue stiffness, the maximum recommended jaw angle for sealing tissue can be selected suitable for the respective tissue stiffness and size. For increasingly stiffer tissues, an increasingly larger maximum recommended jaw angle may be suitable for sealing the stiffer tissue. The control unit 94 can access a suitable look-up table in memory to determine (e.g., via interpolation) a suitable maximum recommended jaw angle for the detected initial contact jaw angle and the detected tissue stiffness. Any of the surgical instruments described herein that are configured to monitor both the current jaw angle 26 and the current clamping force 28 can implement the approach illustrated in FIG. 27.

Figure 28:
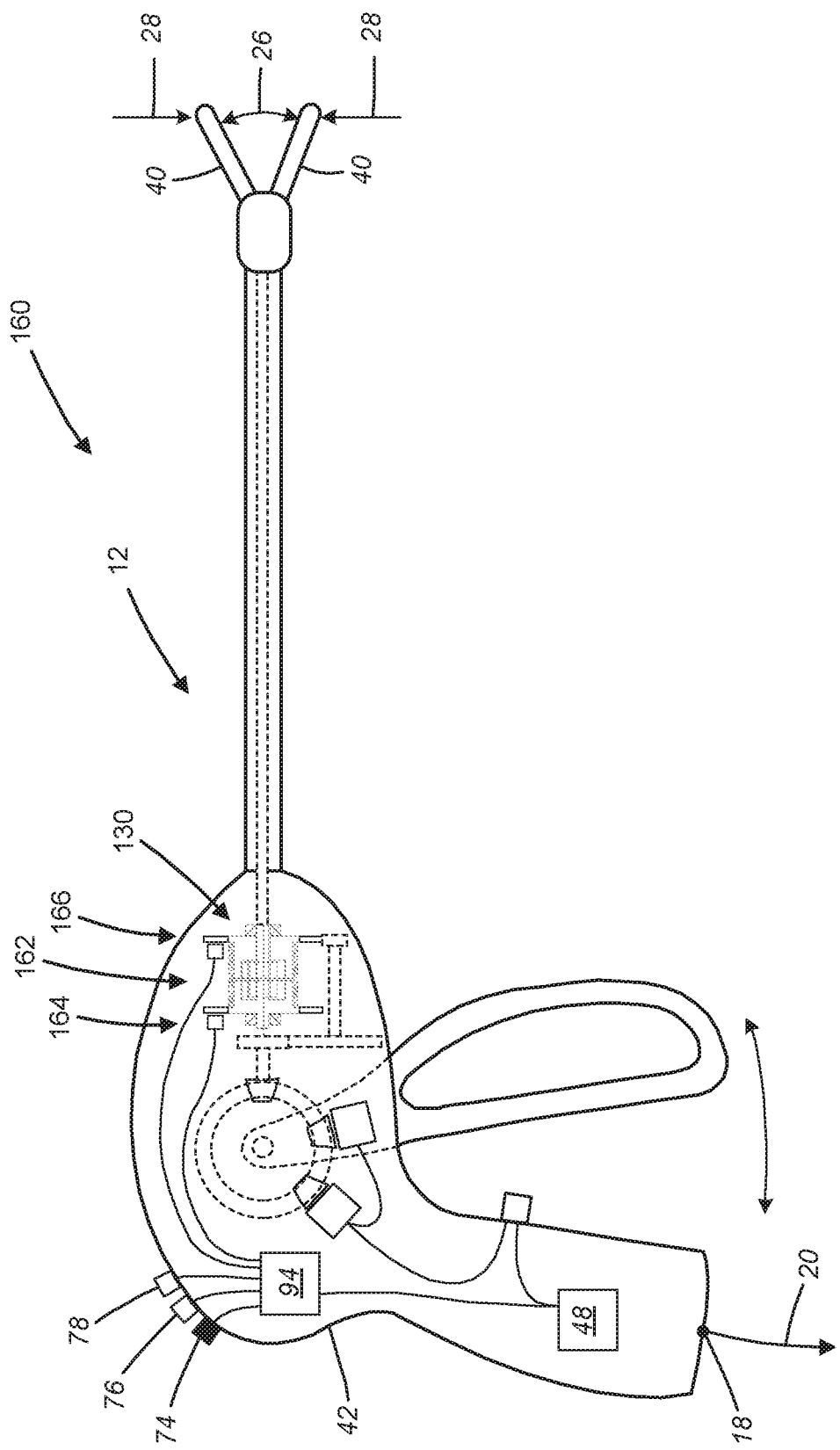
FIG. 28, FIG. 29, and FIG. 30 illustrate a hand held surgical instrument that includes a spring assembly configured to control jaw clamping force, the surgical instrument is configured to monitor jaw angle and jaw clamping force and to provide feedback based on the jaw angle and jaw clamping force regarding whether the jaw angle and/or jaw clamping force is suitable for tissue sealing and/or cutting, in accordance with some embodiments.
Figure 29:
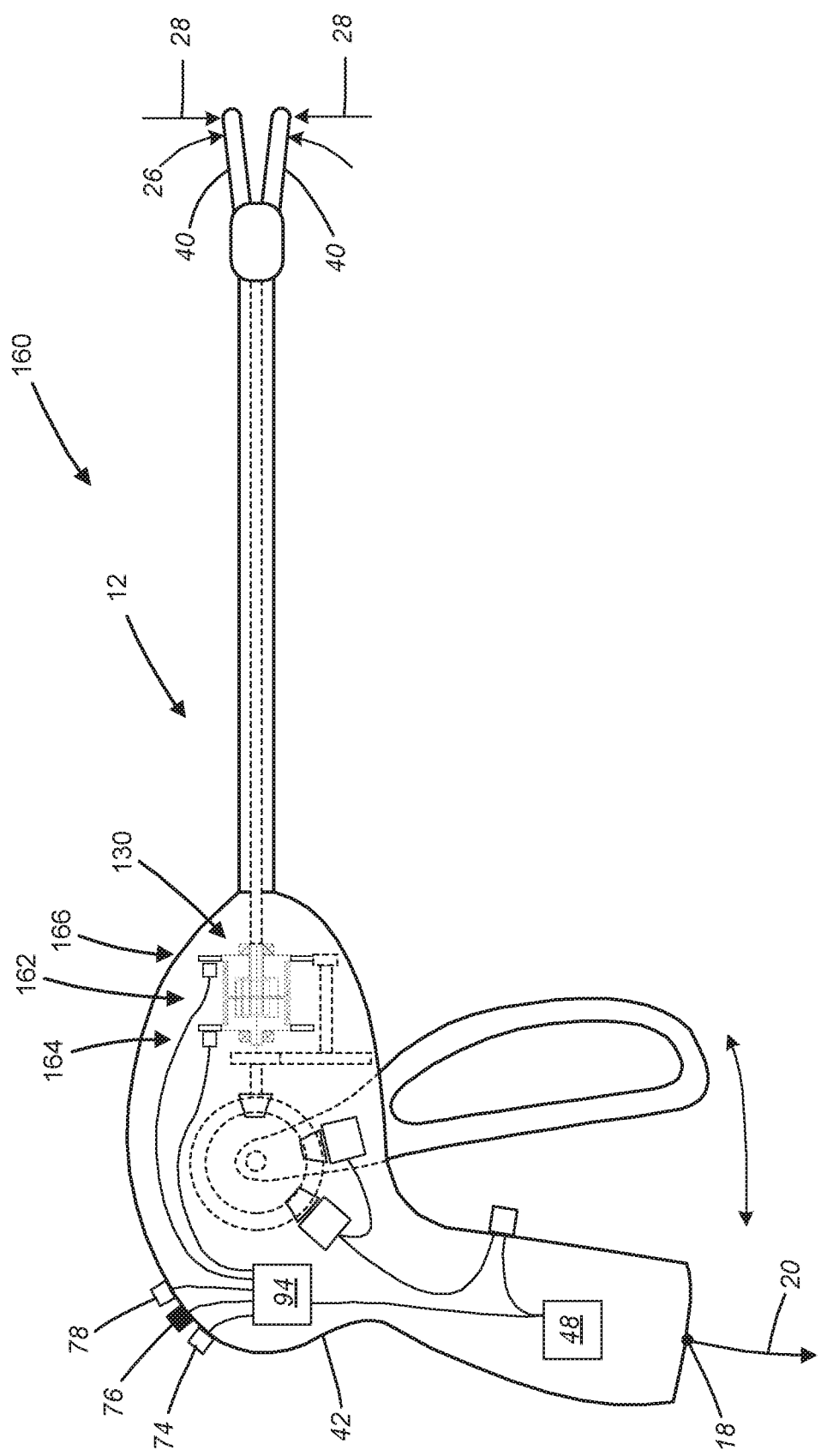
Figure 30:
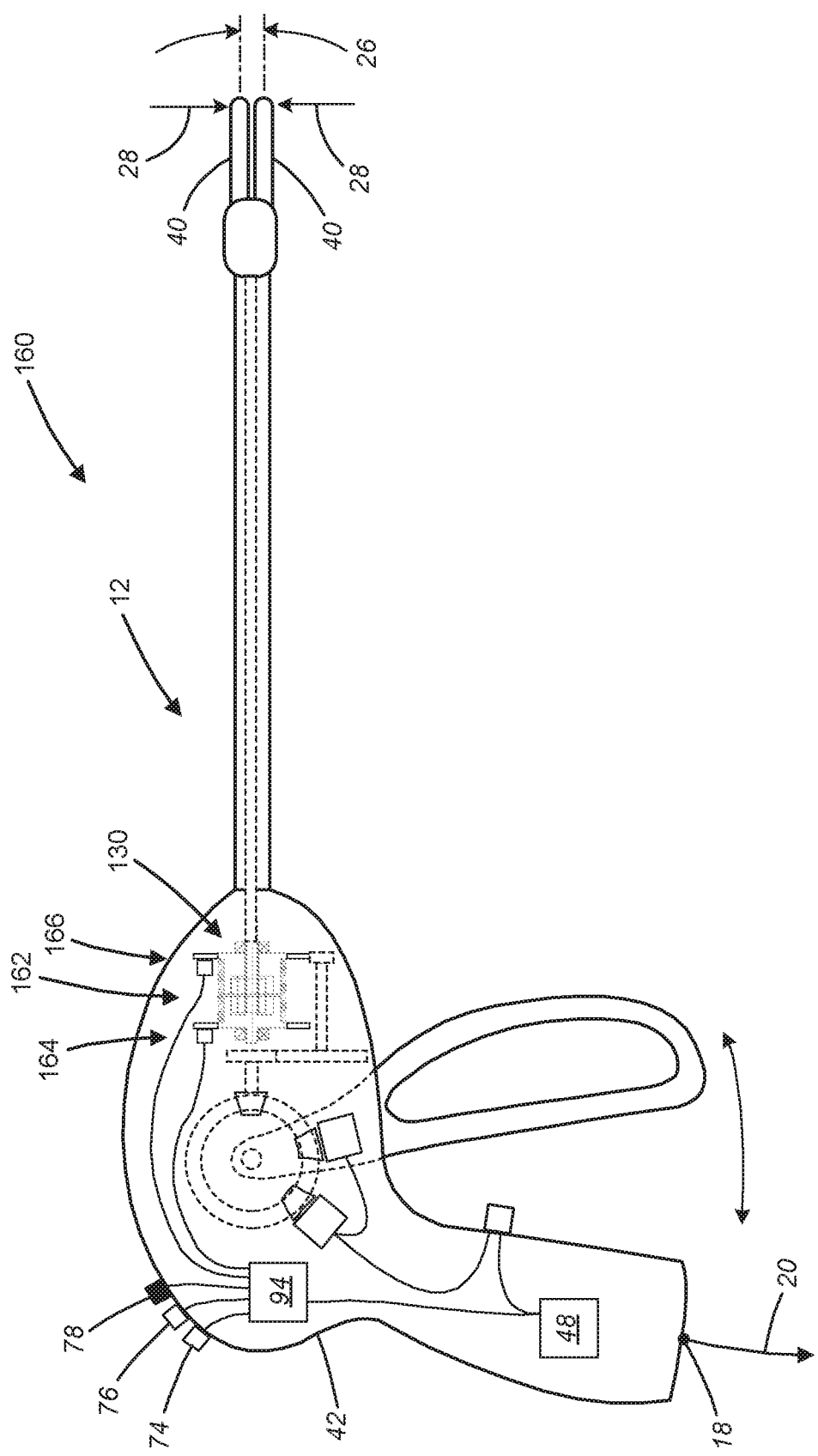

FIG. 28, FIG. 29, and FIG. 30 illustrate a hand held surgical instrument 160 that includes the torsion spring assembly 130 configured to control jaw clamping force. The surgical instrument 160 is configured to monitor the jaw angle 26 and the jaw clamping force 28 and to provide feedback based on the jaw angle 26 and jaw clamping force 28 regarding whether the jaw angle 26 and/or jaw clamping force 28 is suitable for tissue sealing and/or cutting, in accordance with some embodiments. The surgical instrument 160 includes the surgical instrument 12, the control unit 94, and an encoder assembly 162 that monitors the orientation of the input and output links 132, 134 of the torsion spring assembly 130. The encoder assembly 162 includes a first encoder subassembly 164 that monitors the orientation of the output link 134 and a second encoder subassembly 166 that monitors the orientation of the input link 132. The control unit 94 is configured to process the output from the first encoder subassembly 164 to monitor the current jaw angle 26. The control unit 94 compares the output from the first and second encoder subassemblies 164, 166 to monitor relative orientation between the input and output links 132, 134 of the torsion spring assembly 130. The relative orientation between the input and output links 132, 134 is a function of the torque transmitted through the torsion spring assembly 130 and the control unit 94 can be configured to detect when the torque transmitted through the torsion spring assembly 130 produces an orientation difference between the input and output links 132, 134 and to calculate a torque transmitted through the torsion spring assembly 130 based on the orientation difference between the input and output links 132, 134. The control unit 94 can access a suitable look-up table in memory to determine a torsion transmitted through the torsions spring assembly 130 for the detected orientation difference between the input and output links 132, 134.

In the surgical instrument 160, the control unit 94 processes output from the encoder assembly 162 to monitor the current jaw angle 26 and the current clamping force 28. Based on the current jaw angle 26 and the current clamping force 28, the control unit 94 can provide feedback to the operator of the surgical instrument 160 via the feedback output lights 74, 76, 78. As illustrated in FIG. 28, when the current jaw angle 26 and the current clamping force 28 are not suitable for sealing tissue clamped by the jaws 40, the control unit 94 energizes the output light 74. For example, the control unit 94 can be configured to energize the output light 74 if the current jaw angle 26 is greater than a maximum recommended angle for sealing tissue or if the current clamping force 28 is less than a minimum recommended clamping force for sealing tissue. As illustrated in FIG. 29, when the current jaw angle 26 and the current clamping force 28 are suitable for sealing tissue clamped by the jaws 40 and the current jaw angle 26 is greater than a maximum recommended angle for cutting tissue, the control unit 94 energizes the output light 76. For example, the control unit 94 can be configured to energize the output light 76 if the current jaw angle 26 is equal to or less than a maximum recommended angle for sealing tissue, the current clamping force 28 is equal to or greater than a minimum recommended clamping force for sealing tissue, and the current jaw angle 26 is greater than a maximum recommended angle for cutting tissue. As illustrated in FIG. 30, when the current jaw angle 26 and the current clamping force 28 are suitable for sealing tissue clamped by the jaws 40 and the current jaw angle 26 is equal to or less than a maximum recommended angle for cutting tissue, the control unit 94 energizes the output light 78. For example, the control unit 94 can be configured to energize the output light 78 if the current jaw angle 26 is equal to or less than a maximum recommended angle for sealing tissue, the current clamping force 28 is equal to or greater than a minimum recommended clamping force for sealing tissue, and the current jaw angle 26 is equal to or less than the maximum recommended angle for cutting tissue.

The surgical instrument 160 can be configured to include the sealing enablement output 18 and output the sealing enablement signal 20. With the surgical instrument 160, the sealing enablement signal 20 can be indicative of at least one of: (a) the current jaw angle 26 is greater than the maximum recommended clamping angle for sealing tissue clamped by the jaws 40 or the current clamping force 28 is less than the minimum recommended clamping force for sealing tissue clamped by the jaws 40, or (b) the current jaw angle 26 is equal to or less than the maximum recommended clamping angle for sealing tissue clamped by the jaws 40 and the current clamping force 28 is equal to or greater than the minimum recommended clamping force for sealing tissue clamped by the jaws 40. When configured to include the sealing enablement output 18, the surgical instrument 160 can be used in the tissue sealing and cutting system 10 in lieu of the surgical instrument 12.

Figure 31:
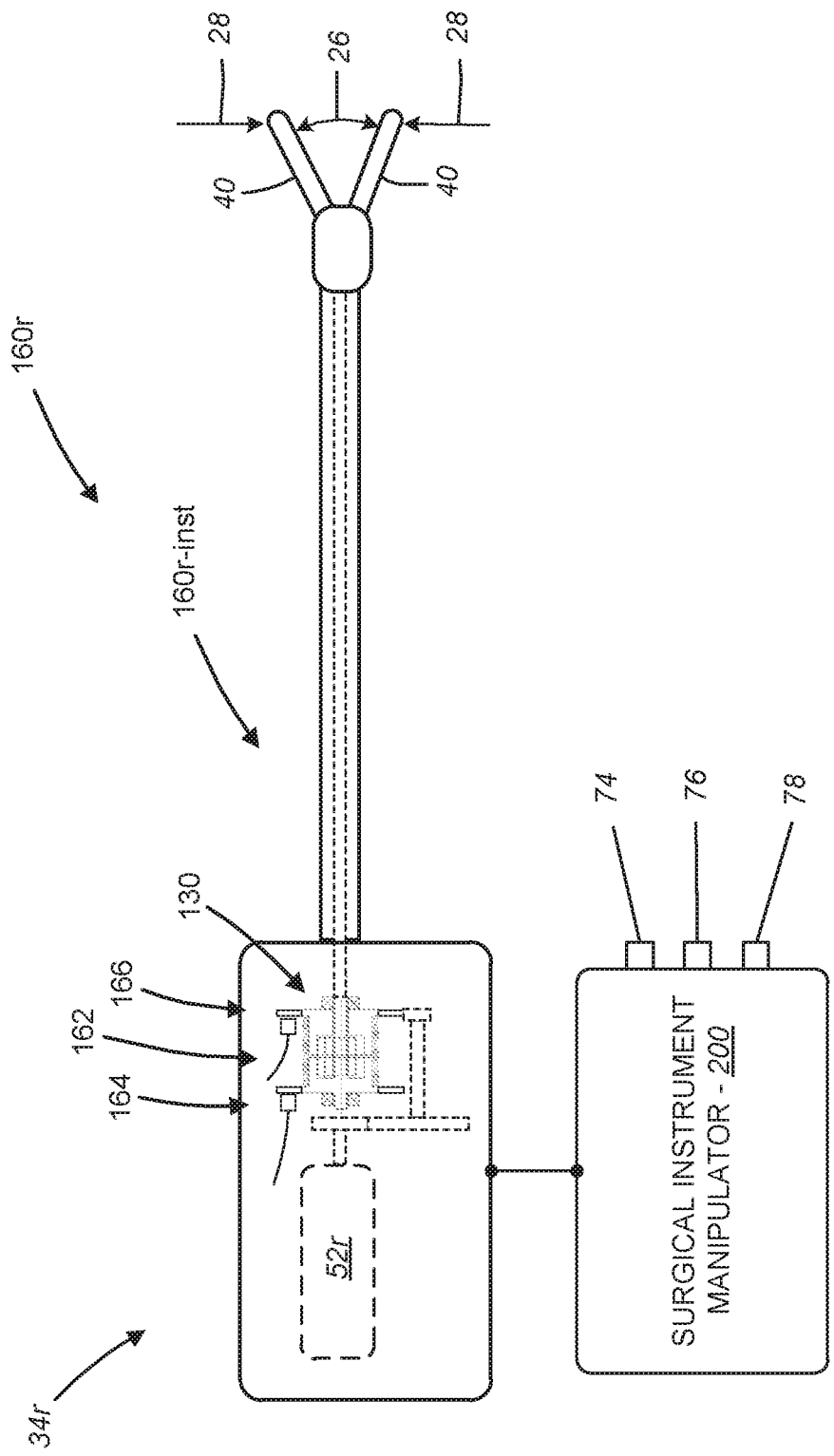
FIG. 31 illustrates a surgical assembly including a spring assembly configured to control jaw clamping force and monitor jaw angle and jaw clamping force and to provide feedback based on the jaw angle and jaw clamping force regarding whether the jaw angle and/or jaw clamping force is suitable for tissue sealing and/or cutting, in accordance with some embodiments.

FIG. 31 illustrates a surgical assembly 160r for tissue sealing and/or cutting, in accordance with some embodiments. The surgical assembly 160r is configured similar to the surgical instrument 160, but includes a surgical instrument 160r-inst and the manipulator 200 to which the surgical instrument 160r-inst is detachably mountable for manipulation by an operator via the manipulator 200. The surgical assembly 160r includes components similar to components of the surgical instrument 160 with the similar components being designated by the same or similar reference numbers and the description of such components of the surgical instrument 160 being applicable to the respective components of the surgical assembly 160r. For example, the surgical assembly 160r includes the torsion spring assembly 130, the encoder assembly 162, and the output lights 74, 76, 78. In some embodiments, the surgical assembly 160r includes a control unit that processes output from the encoder assembly 162 and controls illumination of the output lights 74, 76, 78 to provide the feedback to the operator of the surgical assembly 160r as described herein with respect to the surgical instrument 160.

Figure 32:
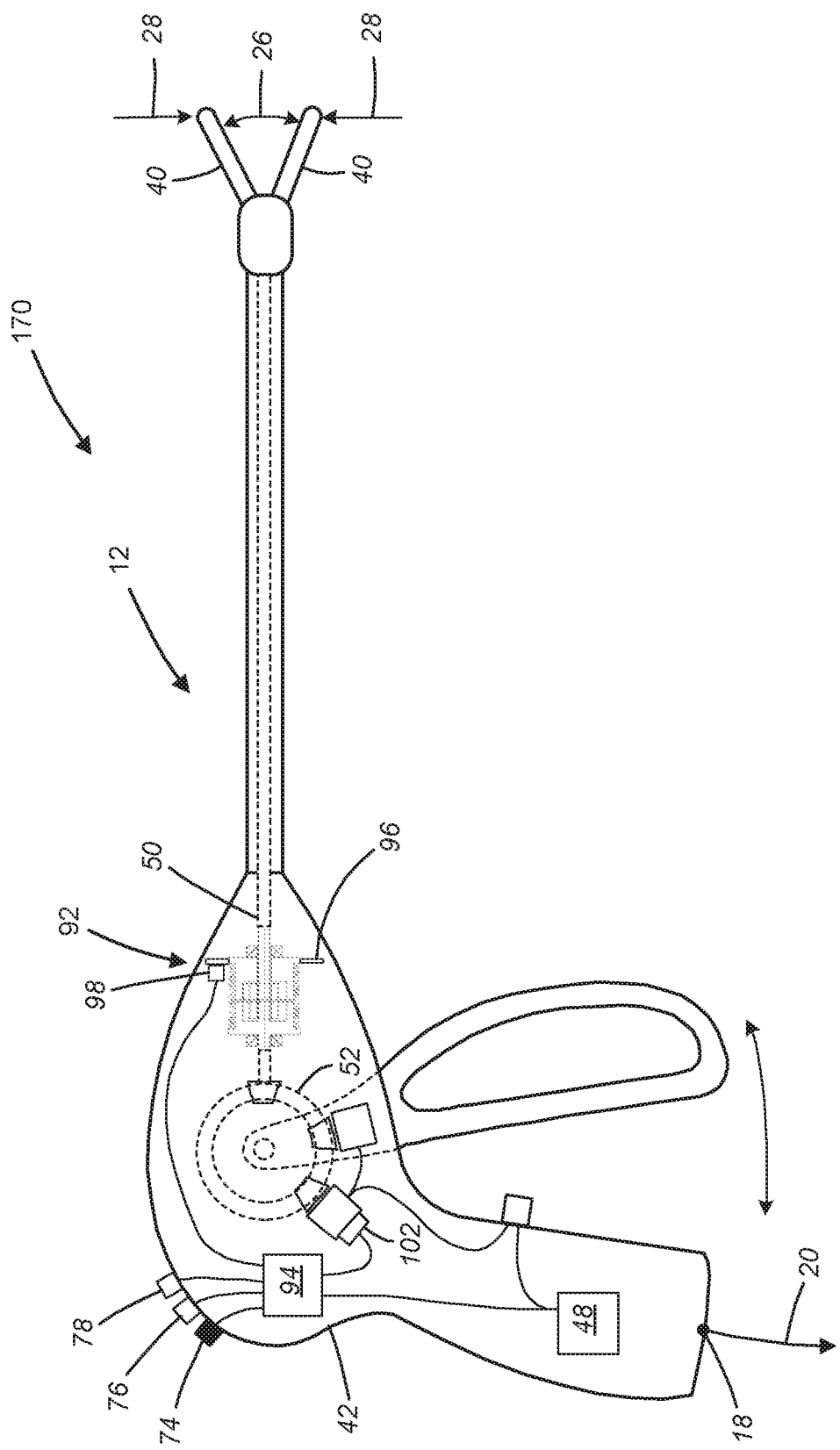
FIG. 32, FIG. 33, and FIG. 34 illustrate another hand held surgical instrument that includes a spring assembly configured to control jaw clamping force, the surgical instrument is configured to monitor jaw angle and jaw clamping force and to provide feedback based on the jaw angle and jaw clamping force regarding whether the jaw angle and/or jaw clamping force is suitable for tissue sealing and/or cutting, in accordance with some embodiments.
Figure 33:
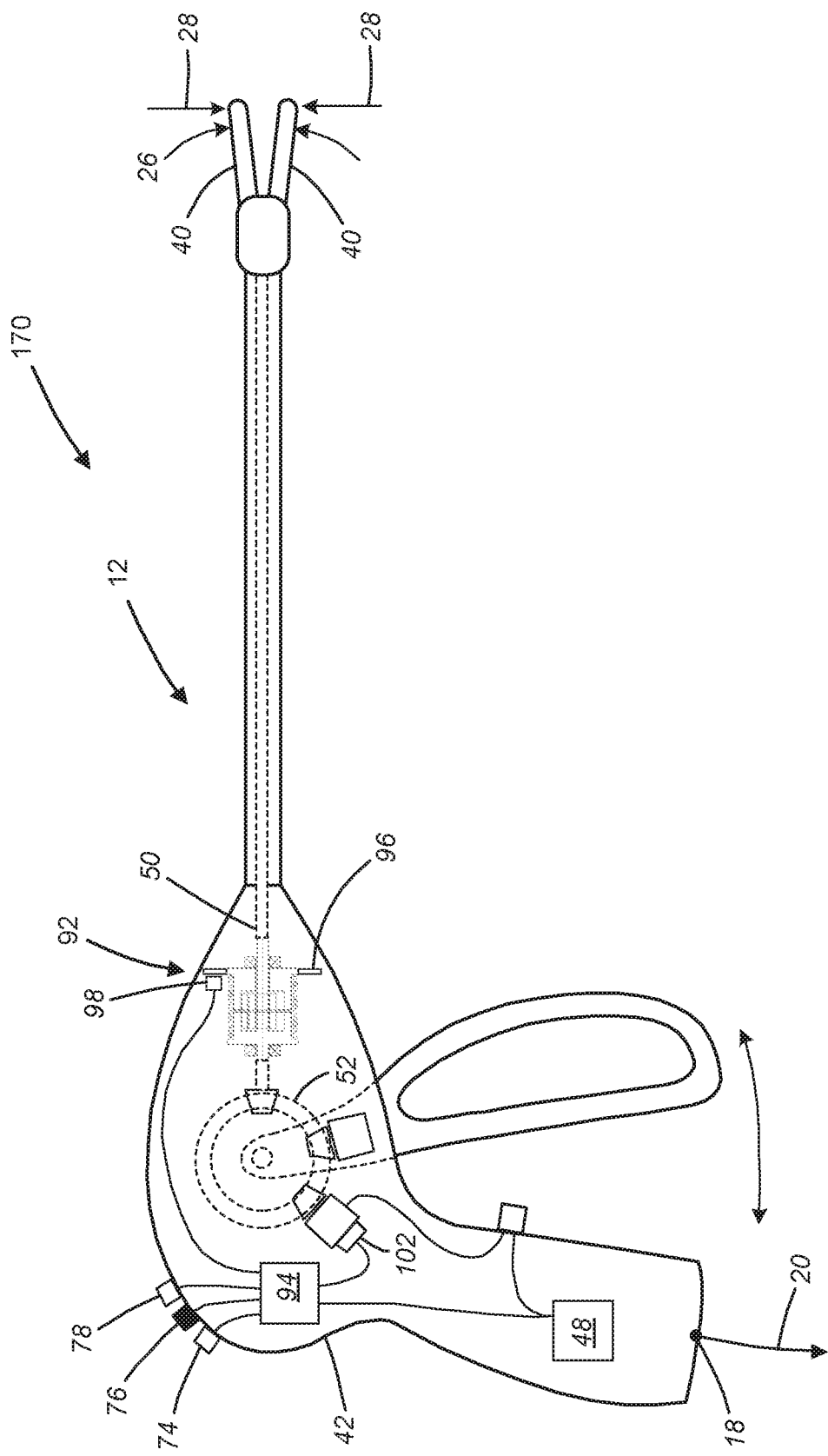
Figure 34:
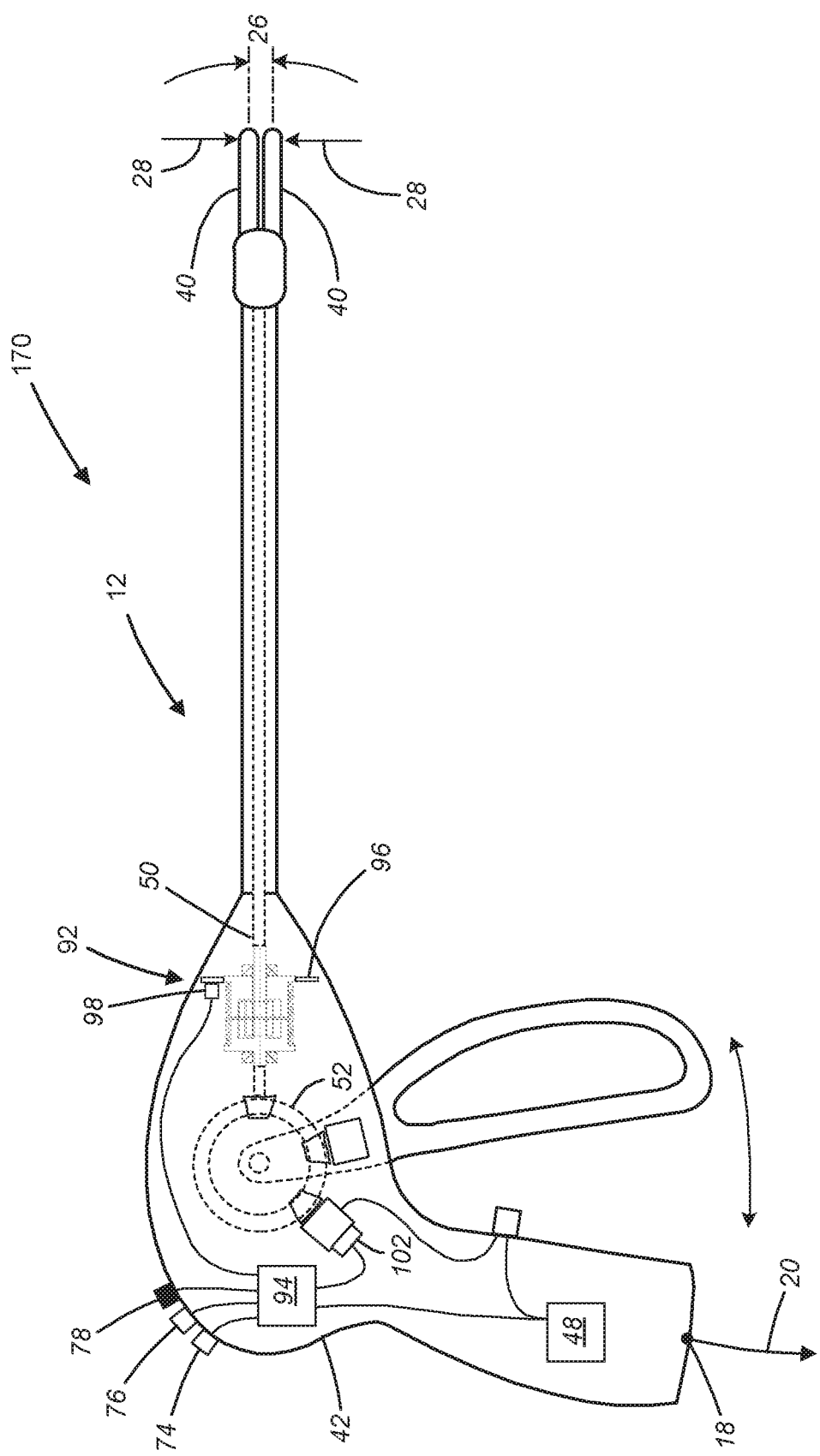

FIG. 32, FIG. 33, and FIG. 34 illustrate a hand held surgical instrument 170 that is configured to monitor the jaw angle 26 and the jaw clamping force 28 and to provide feedback based on the jaw angle 26 and the jaw clamping force 28 regarding whether the jaw angle 26 and/or the jaw clamping force 28 is suitable for tissue sealing and/or cutting, in accordance with some embodiments. The surgical instrument 170 includes the surgical instrument 12, the control unit 94, the torque sensor 102, the torsion spring assembly 130, and the encoder assembly 92. The surgical instrument 170 can include one or more of feedback output lights 74, 76, 78 and/or the sealing enablement output 18. The surgical instrument 170 is configured similar to the surgical instrument 150 except that the surgical instrument 170 further includes the torsion spring assembly 130. The description of the configuration and operation of the surgical instrument 150 and the torsion spring assembly 130 are applicable to the surgical instrument 170. As illustrated in FIG. 23, when the current jaw angle 26 and the current clamping force 28 are not suitable for sealing tissue clamped by the jaws 40, the control unit 94 energizes the output light 74. For example, the control unit 94 can be configured to energize the output light 74 if the current jaw angle 26 is greater than a maximum recommended angle for sealing tissue or if the current clamping force 28 is less than a minimum recommended clamping force for sealing tissue. As illustrated in FIG. 32, when the current jaw angle 26 and the current clamping force 28 are suitable for sealing tissue clamped by the jaws 40 and the current jaw angle 26 is greater than a maximum recommended angle for cutting tissue, the control unit 94 energizes the output light 76. For example, the control unit 94 can be configured to energize the output light 76 if the current jaw angle 26 is equal to or less than a maximum recommended angle for sealing tissue, the current clamping force 28 is equal to or greater than a minimum recommended clamping force for sealing tissue, and the current jaw angle 26 is greater than a maximum recommended angle for cutting tissue. As illustrated in FIG. 33, when the current jaw angle 26 and the current clamping force 28 are suitable for sealing tissue clamped by the jaws 40 and the current jaw angle 26 is equal to or less than a maximum recommended angle for cutting tissue, the control unit 94 energizes the output light 78. For example, the control unit 94 can be configured to energize the output light 78 if the current jaw angle 26 is equal to or less than a maximum recommended angle for sealing tissue, the current clamping force 28 is equal to or greater than a minimum recommended clamping force for sealing tissue, and the current jaw angle 26 is equal to or less than the maximum recommended angle for cutting tissue.

The surgical instrument 170 can be configured to include the sealing enablement output 18 and output the sealing enablement signal 20. With the surgical instrument 170, the sealing enablement signal 20 can be indicative of at least one of: (a) the current jaw angle 26 is greater than the maximum recommended clamping angle for sealing tissue clamped by the jaws 40 or the current clamping force 28 is less than the minimum recommended clamping force for sealing tissue clamped by the jaws 40, or (b) the current jaw angle 26 is equal to or less than the maximum recommended clamping angle for sealing tissue clamped by the jaws 40 and the current clamping force 28 is equal to or greater than the minimum recommended clamping force for sealing tissue clamped by the jaws 40. When configured to include the sealing enablement output 18, the surgical instrument 170 can be used in the tissue sealing and cutting system 10 in lieu of the surgical instrument 12.

The control unit 94 in the various embodiments of the surgical instrument described herein can have any suitable configuration for controlling the respective embodiment as described. For example, the control unit 94 can include one or more processors and memory (e.g., any suitable combination of read only memory (ROM) and/or random access memory (RAM)) for storing instructions and data for operating the embodiment as described). The control unit 94 can include any suitable micro-controller or field-programmable gate array (FPGA).

Figure 35:
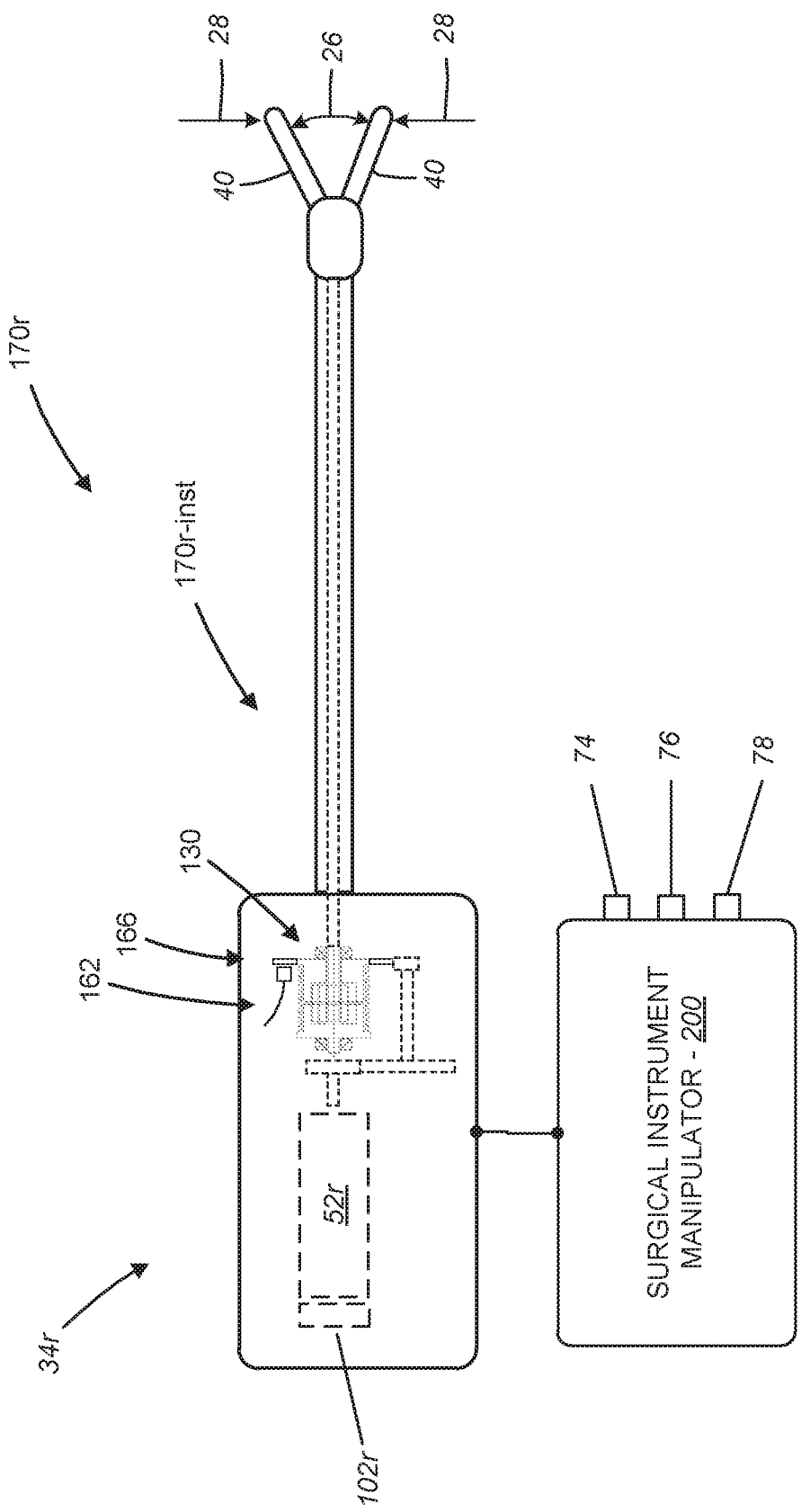
FIG. 35 illustrates a surgical assembly configured to control jaw clamping force, monitor jaw angle and jaw clamping force, and provide feedback based on the jaw angle and jaw clamping force regarding whether the jaw angle and/or jaw clamping force is suitable for tissue sealing and/or cutting, in accordance with some embodiments.

FIG. 35 illustrates a surgical assembly 170r for tissue sealing and/or cutting, in accordance with some embodiments. The surgical assembly 170r is configured similar to the surgical instrument 170, but includes a surgical instrument 170r-inst and the manipulator 200 to which the surgical instrument 170r-inst is detachably mountable for manipulation by an operator via the manipulator 200. The surgical assembly 170r includes components similar to components of the surgical instrument 170 with the similar components being designated by the same or similar reference numbers and the description of such components of the surgical instrument 170 being applicable to the respective components of the surgical assembly 170r. For example, surgical assembly 170r includes the torsion spring assembly 130, the encoder assembly 162, a torque sensor 102r (which is configured similar to the torque sensor 102 of the surgical instrument 170), the output lights 74, 76, 78, and a control unit that processes output from the encoder assembly 162 and the torque sensor 102r, and controls illumination of the output lights 74, 76, 78 to provide the feedback to the operator of the surgical assembly 170r as described herein with respect to the surgical instrument 170.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument for sealing and cutting tissue, the surgical instrument comprising:
   an end effector comprising a jaw and a knife, wherein the end effector is configured to actuate the jaw to clamp tissue in response to an input from an operator of the surgical instrument, and wherein the end effector is configured to receive a sealing energy to seal tissue clamped by the jaw;
   a sealing energy generator operable to output the sealing energy to the end effector;
   a spring assembly comprising an output link drivingly coupled with the jaw, an input link, and a spring coupled with the input and output links to transfer an articulation force from the input link to the output link to induce a grip force of the jaw, the spring being preloaded to inhibit relative movement between the input link and the output link while the transferred articulation force is below a predetermined level and to allow relative movement between the input link and the output link when the transferred articulation force is above the predetermined level;
   an actuation monitoring assembly that generates at least one of a jaw-angle output indicative of a current clamping angle of the jaw and a clamping-force output indicative of a current clamping force of the jaw; and
   a feedback assembly that outputs to the operator of the surgical instrument, in response to at least one of the jaw-angle output and the clamping-force output, one or more indications comprising at least one of:
      an indication that the current clamping angle is greater than a maximum recommended clamping angle for sealing tissue clamped by the jaw;
      an indication that the current clamping angle is equal to or less than the maximum recommended clamping angle for sealing tissue clamped by the jaw;
      an indication that the current clamping angle is greater than a maximum recommended clamping angle for cutting tissue clamped by the jaw;
      an indication that the current clamping angle is equal to or less than the maximum recommended clamping angle for cutting tissue clamped by the jaw;
      an indication that the current clamping force is less than a minimum recommended clamping force for sealing tissue clamped by the jaw; and
      an indication that the current clamping force is equal to or greater than the minimum recommended clamping force for sealing tissue clamped by the jaw.

2. The surgical instrument of claim 1, wherein:
   the actuation monitoring assembly generates the jaw-angle output; and
   the feedback assembly outputs to the operator at least one of:
      the indication that the current clamping angle is greater than the maximum recommended clamping angle for cutting tissue clamped by the jaw; and
      the indication that the current clamping angle is equal to or less than the maximum recommended clamping angle for cutting tissue clamped by the jaw.

3. The surgical instrument of claim 1, wherein:
   the actuation monitoring assembly generates the jaw-angle output; and
   the feedback assembly outputs to the operator at least one of:
      the indication that the current clamping angle is greater than the maximum recommended clamping angle for sealing tissue clamped by the jaw; and
      the indication that the current clamping angle is equal to or less than the maximum recommended clamping angle for sealing tissue clamped by the jaw.

4. The surgical instrument of claim 1, wherein:
   the actuation monitoring assembly generates the clamping-force output; and
   the feedback assembly outputs to the operator at least one of:
      the indication that the current clamping force is less than the minimum recommended clamping force for sealing tissue clamped by the jaw; and
      the indication that the current clamping force is equal to or greater than the minimum recommended clamping force for sealing tissue clamped by the jaw.

5. The surgical instrument of claim 1, wherein:
   the actuation monitoring assembly generates the jaw-angle output and the clamping-force output; and
   the feedback assembly outputs to the operator at least one of:
      the indication that the current clamping angle is greater than the maximum recommended clamping angle for sealing tissue clamped by the jaw; and
      the indication that the current clamping angle is equal to or less than the maximum recommended clamping angle for sealing tissue clamped by the jaw; and
   the feedback assembly comprises a control unit that:

monitors the jaw-angle output and the clamping-force output to identify an initial contact jaw angle corresponding to initial contact between the jaw and tissue clamped by the jaw; and selects the maximum recommended clamping angle for sealing tissue clamped by the jaw based on the initial contact jaw angle.

6. The surgical instrument of claim 5, wherein the control unit:

processes the jaw-angle output and the clamping-force output to determine a tissue stiffness of the tissue clamped by the jaw; and selects the maximum recommended clamping angle for sealing tissue clamped by the jaw based on the tissue stiffness.

7. The surgical instrument of claim 1, wherein the feedback assembly comprises one or more output elements that output the one or more indications to the operator, the one or more output elements comprising at least one of:

one or more indicator lights;

an output display; and an aural output device.

8. The surgical instrument of claim 1, comprising a sealing enablement output that outputs a sealing enablement signal for controlling enablement of supply of a sealing energy to the surgical instrument for sealing tissue clamped by the jaw, the sealing enablement signal being indicative of at least one of:

the current clamping angle is greater than the maximum recommended clamping angle for sealing tissue clamped by the jaw;

the current clamping angle is equal to or less than the maximum recommended clamping angle for sealing tissue clamped by the jaw;

the current clamping force is less than the minimum recommended clamping force for sealing tissue clamped by the jaw; and the current clamping force is equal to or greater than the minimum recommended clamping force for sealing tissue clamped by the jaw.

9. The surgical instrument of claim 1, further comprising a hand-operated lever configured to be actuated by the operator to generate the input from the operator, and wherein the hand-operated lever is drivingly coupled with the jaw for articulation of the jaw to grasp tissue and to clamp tissue.

10. The surgical instrument of claim 1, further comprising a drive input that can be coupled to a motor of a teleoperated surgical system, wherein the drive input is drivingly coupled with the jaw to actuate the jaw.

* * * * *